US009526580B2

(12) United States Patent
Humayun et al.

(10) Patent No.: US 9,526,580 B2
(45) Date of Patent: Dec. 27, 2016

(54) STERILE SURGICAL TRAY

(71) Applicant: DOHENY EYE INSTITUTE, Los Angeles, CA (US)

(72) Inventors: Mark Humayun, Glendale, CA (US); Charles DeBoer, Altadena, CA (US); Matthew McCormick, Forest Falls, CA (US); Prashant Bhadri, Pico Rivera, CA (US); Joel Cicchella, Los Angeles, CA (US); Ralph Kerns, Laguna Niguel, CA (US)

(73) Assignee: Doheny Eye Institute, Los Angeles, CA (US)

( * ) Notice: Subject to any disclaimer, the term of this patent is extended or adjusted under 35 U.S.C. 154(b) by 0 days.

(21) Appl. No.: 14/165,473

(22) Filed: Jan. 27, 2014

(65) Prior Publication Data

US 2014/0378952 A1     Dec. 25, 2014

Related U.S. Application Data

(63) Continuation of application No. 12/684,850, filed on Jan. 8, 2010, now abandoned, which is a
(Continued)

(51) Int. Cl.
*A61F 2/16*       (2006.01)
*A61B 19/02*     (2006.01)
(Continued)

(52) U.S. Cl.
CPC .......... *A61B 19/0271* (2013.01); *A61B 50/13* (2016.02); *A61B 50/33* (2016.02); *A61B 90/40* (2016.02);
(Continued)

(58) Field of Classification Search
CPC ............... A61B 19/38; A61B 19/0271; A61B 19/00736; A61B 19/5202; A61B 2017/00973; A61B 2017/00544; A61B 2017/00734; A61B 2017/00225; A61B 2019/025; A61B 2019/0278; A61B 2019/448; A61F 9/00763; A61M 3/0262; A61M 2205/3561; A61M 2205/123; A61M 2205/505; A61M 2205/3553
(Continued)

(56) References Cited

U.S. PATENT DOCUMENTS 3,116,828 A    1/1964   Glassman
3,293,430 A    12/1966  Wustner
(Continued)

FOREIGN PATENT DOCUMENTS

CN     2289530 Y      9/1998
EP     0 876 799 A2   11/1998
(Continued)

OTHER PUBLICATIONS

U.S. Pat. No. 8,177,064 including its prosecution history, the references cited therein and the Office Actions therein.
(Continued)

*Primary Examiner* — Ashley Fishback
(74) *Attorney, Agent, or Firm* — Baker Botts L.L.P.

(57) ABSTRACT

A sterile surgical tray includes structure for receiving a plurality of surgical instruments. The sterile surgical tray also may include electrical input and output connectors attached to tray.

32 Claims, 19 Drawing Sheets

Related U.S. Application Data continuation-in-part of application No. 12/256,420, filed on Oct. 22, 2008, now Pat. No. 8,323,271, which is a continuation-in-part of application No. 12/107,038, filed on Apr. 21, 2008, now Pat. No. 8,177,776, said application No. 12/256,420 is a continuation-in-part of application No. 12/107,052, filed on Apr. 21, 2008, now abandoned, said application No. 12/256,420 is a continuation-in-part of application No. 12/106,962, filed on Apr. 21, 2008, now Pat. No. 8,177,064, said application No. 12/684,850 is a continuation-in-part of application No. 12/107,038, filed on Apr. 21, 2008, now Pat. No. 8,177,776, said application No. 12/684,850 is a continuation-in-part of application No. 12/107,052, filed on Apr. 21, 2008, now abandoned, said application No. 12/684,850 is a continuation-in-part of application No. 12/106,962, filed on Apr. 21, 2008, now Pat. No. 8,177,064.

(60) Provisional application No. 60/925,546, filed on Apr. 20, 2007, provisional application No. 60/925,562, filed on Apr. 20, 2007, provisional application No. 60/925,548, filed on Apr. 20, 2007.

(51) Int. Cl.
  *A61F 9/007* (2006.01)
  *A61M 3/02* (2006.01)
  *A61B 17/00* (2006.01)

(52) U.S. Cl.
  CPC ........... *A61B 90/98* (2016.02); *A61F 9/00736* (2013.01); *A61M 3/0262* (2013.01); *A61B 90/30* (2016.02); *A61B 2017/00225* (2013.01); *A61B 2017/00544* (2013.01); *A61B 2017/00734* (2013.01); *A61B 2017/00973* (2013.01); *A61B 2050/3008* (2016.02); *A61F 9/00763* (2013.01); *A61M 2205/123* (2013.01); *A61M 2205/3553* (2013.01); *A61M 2205/3561* (2013.01); *A61M 2205/505* (2013.01); *Y10T 137/8376* (2015.04); *Y10T 137/86035* (2015.04)

(58) Field of Classification Search
  USPC ......... 433/77, 79, 98–101; 604/22; 606/107, 606/171, 174; 623/6.12, 905
  See application file for complete search history.

(56) References Cited

U.S. PATENT DOCUMENTS

| | | |
|---|---|---|
| 3,304,609 A | 2/1967 | Horowitz et al. |
| 3,366,230 A | 1/1968 | Loran |
| 3,702,940 A | 11/1972 | Stewart |
| 3,820,656 A | 6/1974 | Orr |
| 3,884,238 A | 5/1975 | O'Malley et al. |
| 3,976,195 A | 8/1976 | Cohen |
| 3,986,263 A | 10/1976 | Borgelt et al. |
| 4,011,944 A | 3/1977 | Cooley et al. |
| 4,014,342 A | 3/1977 | Staub et al. |
| 4,019,514 A | 4/1977 | Banko |
| 4,108,182 A | 8/1978 | Hartman et al. |
| 4,112,947 A | 9/1978 | Nehring |
| 4,117,843 A | 10/1978 | Banko |
| 4,266,669 A | 5/1981 | Watson |
| 4,288,733 A | 9/1981 | Bilanceri et al. |
| 4,293,074 A | 10/1981 | Dunsky |
| 4,320,761 A | 3/1982 | Haddad |
| 4,324,243 A | 4/1982 | Helfgott et al. |
| 4,378,108 A | 3/1983 | Bailey, Jr. |
| 4,428,748 A | 1/1984 | Peyman et al. |
| 4,430,062 A | 2/1984 | Henrichsen et al. |
| 4,479,762 A | 10/1984 | Bilstad et al. |
| 4,735,610 A | 4/1988 | Akkas et al. |
| 4,798,580 A | 1/1989 | DeMeo et al. |
| 4,869,266 A | 9/1989 | Taylor et al. |
| 4,889,231 A | 12/1989 | Foote et al. |
| 4,903,710 A | 2/1990 | Jessamine et al. |
| 4,930,997 A | 6/1990 | Bennett |
| 4,974,728 A | 12/1990 | Colton |
| 5,007,535 A | 4/1991 | Meseke et al. |
| 5,013,240 A | 5/1991 | Bailey et al. |
| 5,078,677 A | 1/1992 | Gentelia et al. |
| 5,392,917 A | 2/1995 | Alpern et al. |
| 5,399,007 A | 3/1995 | Marconet |
| 5,433,702 A | 7/1995 | Zelman et al. |
| 5,455,766 A | 10/1995 | Scheller et al. |
| 5,464,025 A | 11/1995 | Charles et al. |
| 5,508,836 A | 4/1996 | DeCaro et al. |
| 5,554,097 A | 9/1996 | Guy |
| 5,586,163 A | 12/1996 | Goldstein |
| 5,627,584 A | 5/1997 | Nishikori et al. |
| 5,746,719 A | 5/1998 | Farra et al. |
| 5,779,053 A | 7/1998 | Partika et al. |
| 5,873,717 A | 2/1999 | Behringer |
| 5,910,110 A | 6/1999 | Bastable |
| 5,989,262 A | 11/1999 | Josephberg |
| 6,022,088 A | 2/2000 | Metzler |
| 6,024,699 A | 2/2000 | Surwit et al. |
| 6,051,011 A | 4/2000 | Weidenbenner |
| 6,059,792 A | 5/2000 | Josephberg |
| 6,059,795 A | 5/2000 | Wallace et al. |
| 6,074,399 A | 6/2000 | Wallace et al. |
| 6,102,044 A | 8/2000 | Naidyhorski |
| 6,117,127 A | 9/2000 | Helmreich et al. |
| 6,158,437 A | 12/2000 | Vagley |
| 6,185,096 B1 | 2/2001 | Helot et al. |
| 6,206,014 B1 | 3/2001 | Cameron, III et al. |
| 6,217,584 B1 | 4/2001 | Nun |
| 6,251,113 B1 | 6/2001 | Appelbaum et al. |
| 6,258,111 B1 | 7/2001 | Ross et al. |
| 6,282,442 B1 | 8/2001 | Destefano et al. |
| 6,312,258 B1 | 11/2001 | Ashman |
| 6,355,047 B1 | 3/2002 | Wallace et al. |
| 6,405,863 B1 | 6/2002 | Dhindsa |
| 6,428,487 B1 | 8/2002 | Burdorff |
| 6,508,823 B1 | 1/2003 | Gonon |
| 6,579,255 B2 | 6/2003 | Kadziauskas et al. |
| 6,616,606 B1 | 9/2003 | Petersen et al. |
| 6,623,500 B1 | 9/2003 | Cook et al. |
| 6,641,039 B2 | 11/2003 | Southard |
| 6,648,223 B2 | 11/2003 | Boukhny et al. |
| 6,666,875 B1 | 12/2003 | Sakurai et al. |
| 6,716,219 B1 | 4/2004 | Koch |
| 6,769,546 B2 | 8/2004 | Busch |
| 6,896,141 B2 | 5/2005 | McMichael et al. |
| 6,945,981 B2 | 9/2005 | Donofrio et al. |
| 7,100,771 B2 | 9/2006 | Massengale et al. |
| 7,114,500 B2 | 10/2006 | Bonutti |
| 7,165,555 B2 | 1/2007 | Lee |
| 7,267,246 B2 | 9/2007 | Eiskant et al. |
| 7,331,463 B2 | 2/2008 | Hickey |
| 7,362,228 B2 | 4/2008 | Nycz et al. |
| 7,401,703 B2 | 7/2008 | McMichael et al. |
| 7,431,157 B2 | 10/2008 | Porret et al. |
| 7,578,391 B2 | 8/2009 | Nakamura |
| 7,604,007 B1 | 10/2009 | Wooley |
| D626,238 S | 10/2010 | Zinnanti |
| 8,002,783 B2 | 8/2011 | Vercellotti et al. |
| 8,177,064 B2 | 5/2012 | McCormick et al. |
| 8,177,776 B2 | 5/2012 | Humayun et al. |
| 8,323,271 B2 | 12/2012 | Humayun et al. |
| 8,444,629 B2 | 5/2013 | Manna et al. |
| 8,496,681 B2 | 7/2013 | Easley |
| 8,525,059 B2 | 9/2013 | Berger et al. |
| 8,568,391 B2 | 10/2013 | Kerns et al. |
| 8,623,000 B2 | 1/2014 | Humayun et al. |
| 2001/0022615 A1 | 9/2001 | Fernandez et al. |
| 2002/0013517 A1 | 1/2002 | West et al. |

(56) References Cited

U.S. PATENT DOCUMENTS

| | | | |
|---|---|---|---|
| 2003/0068596 A1* | 4/2003 | Castellini | A61C 1/0015 433/98 |
| 2003/0093503 A1 | 5/2003 | Yamaki et al. | |
| 2003/0159969 A1 | 8/2003 | McMichael et al. | |
| 2003/0165794 A1 | 9/2003 | Matoba | |
| 2003/0178488 A1 | 9/2003 | Southard | |
| 2003/0205233 A1 | 11/2003 | Aboul-Hosn et al. | |
| 2004/0004019 A1 | 1/2004 | Busch | |
| 2004/0036386 A1 | 2/2004 | Olivera | |
| 2004/0116952 A1 | 6/2004 | Sakurai et al. | |
| 2004/0138518 A1 | 7/2004 | Rise et al. | |
| 2004/0139048 A1 | 7/2004 | Kerr, II et al. | |
| 2004/0186683 A1 | 9/2004 | Farber et al. | |
| 2004/0208780 A1 | 10/2004 | Faries, Jr. et al. | |
| 2004/0243147 A1 | 12/2004 | Lipow | |
| 2005/0128987 A1 | 6/2005 | Liang | |
| 2005/0245888 A1 | 11/2005 | Cull | |
| 2005/0283138 A1 | 12/2005 | Tashiro et al. | |
| 2006/0002258 A1 | 1/2006 | Nakamura et al. | |
| 2006/0046226 A1 | 3/2006 | Bergler et al. | |
| 2006/0086634 A1 | 4/2006 | Steppe | |
| 2006/0095066 A1 | 5/2006 | Chang et al. | |
| 2006/0100497 A1 | 5/2006 | Sawazaki et al. | |
| 2006/0109105 A1 | 5/2006 | Varner et al. | |
| 2006/0119481 A1 | 6/2006 | Tethrake et al. | |
| 2006/0142739 A1 | 6/2006 | DiSilestro et al. | |
| 2006/0244593 A1 | 11/2006 | Nycz et al. | |
| 2006/0255938 A1 | 11/2006 | Van den Brink | |
| 2006/0272979 A1 | 12/2006 | Lubbers et al. | |
| 2006/0289016 A1 | 12/2006 | Kammer et al. | |
| 2007/0282353 A1 | 12/2007 | Surti et al. | |
| 2007/0290654 A1 | 12/2007 | Govari et al. | |
| 2008/0030345 A1 | 2/2008 | Austin et al. | |
| 2008/0041282 A1 | 2/2008 | Goschy et al. | |
| 2008/0120137 A1 | 5/2008 | Nyholm | |
| 2008/0125761 A1 | 5/2008 | Weston et al. | |
| 2008/0167644 A1 | 7/2008 | Shelton et al. | |
| 2008/0208233 A1 | 8/2008 | Barnes et al. | |
| 2008/0272023 A1 | 11/2008 | McCormick | |
| 2008/0281254 A1 | 11/2008 | Humayun et al. | |
| 2008/0281301 A1 | 11/2008 | DeBoer et al. | |
| 2008/0308698 A1 | 12/2008 | Steppe | |
| 2009/0143734 A1 | 6/2009 | Humayun et al. | |
| 2010/0134303 A1 | 6/2010 | Perkins | |
| 2010/0174415 A1 | 7/2010 | Humayun et al. | |
| 2011/0112518 A1 | 5/2011 | Stanton | |
| 2011/0190690 A1 | 8/2011 | Humayun et al. | |
| 2011/0276340 A1 | 11/2011 | DeBoer et al. | |
| 2011/0295193 A1 | 12/2011 | Fitzgerald et al. | |
| 2012/0232540 A1 | 9/2012 | Baur et al. | |
| 2013/0009606 A1 | 1/2013 | Smith et al. | |
| 2014/0238890 A1 | 8/2014 | Kerns et al. | |
| 2014/0323813 A1 | 10/2014 | Humayun et al. | |
| 2014/0365235 A1 | 12/2014 | DeBoer et al. | |
| 2014/0378952 A1 | 12/2014 | Humayun et al. | |
| 2015/0144514 A1 | 5/2015 | Brennan et al. | |
| 2015/0148615 A1 | 5/2015 | Brennan et al. | |

FOREIGN PATENT DOCUMENTS

| | | | |
|---|---|---|---|
| EP | 1 236 439 | | 9/2002 |
| EP | 1 813 199 A1 | | 8/2007 |
| EP | 2 441 393 | | 4/2012 |
| FI | WO 2009156591 A1 * | 12/2009 | A61B 6/04 |
| JP | 05-044111 U | | 6/1993 |
| JP | 2004-250108 | | 6/1993 |
| JP | 2002-515293 | | 5/2002 |
| JP | 3310360 | | 5/2002 |
| JP | 3088841 | | 10/2002 |
| JP | 2004-081867 A | | 3/2004 |
| JP | 2005-046412 | | 2/2005 |
| JP | 2006-511285 A | | 4/2006 |
| JP | 2007-501055 | | 1/2007 |
| JP | 2009-219718 | | 10/2009 |
| JP | 2010-503513 | | 2/2010 |
| WO | WO 92/20310 | | 11/1992 |
| WO | WO 95/01135 | | 1/1995 |
| WO | WO 98/06338 | | 2/1998 |
| WO | WO 99/59510 A1 | | 11/1999 |
| WO | WO 99/66444 | | 12/1999 |
| WO | WO 00/32115 | | 6/2000 |
| WO | WO 00/32123 | | 6/2000 |
| WO | WO 01/12098 | | 2/2001 |
| WO | WO 02/083021 | | 10/2002 |
| WO | WO 03/034213 | | 4/2003 |
| WO | WO 03/034213 A2 | | 4/2003 |
| WO | WO 2004/060184 A1 | | 7/2004 |
| WO | WO 2004/105631 | | 12/2004 |
| WO | WO 2005/016183 A1 | | 2/2005 |
| WO | WO 2008/036453 A2 | | 3/2008 |
| WO | WO 2008/131357 A1 | | 10/2008 |
| WO | WO 2008/152378 | | 12/2008 |
| WO | 2009/156591 | | 12/2009 |
| WO | WO 2010/030850 | | 3/2010 |

OTHER PUBLICATIONS

U.S. Pat. No. 8,177,776 including its prosecution history, the references cited therein and the Office Actions therein.

U.S. Pat. No. 8,323,271 including its prosecution history, the references cited therein and the Office Actions therein.

U.S. Pat. No. 8,623,000 including its prosecution history, the references cited therein and the Office Actions therein., Aug. 4, 2011.

U.S. Patent Publication No. 2008-0281301, including its prosecution history, the references cited therein and the Office Actions therein.

U.S. Patent Publication No. 2010-0174415 A1, including its prosecution history, the references cited therein and the Office Actions therein.

U.S. Patent Publication No. 2011-0276340, including its prosecution history, the references cited therein and the Office Actions therein.

Extended European Search Report dated Nov. 23, 2010 for European Application No. 08746468.1, filed Apr. 21, 2008.

International Preliminary Report on Patentability and Written Opinion dated Apr. 26, 2011 in PCT Application No. PCT/US2008/080832, filed on Oct. 22, 2008.

International Preliminary Report on Patentability and Written Opinion dated Oct. 20, 2009 in PCT Application No. PCT/US2008/061058, filed on Apr. 21, 2008.

International Search Report and Written Opinion dated Aug. 27, 2008 for PCT Application PCT/US2008/061058, filed Apr. 21, 2008.

International Search Report and Written Opinion dated Dec. 22, 2008 in PCT Application No. PCT/US08/061065, filed on Apr. 21, 2008.

International Search Report and Written Opinion dated Jul. 29, 2010 in PCT Application No. PCT/US2008/080832, filed Oct. 22, 2008.

International Search Report and Written Opinion dated Jun. 2, 2011 in PCT Application No. PCT/US2011/020415 filed Jan. 6, 2011.

International Search Report and Written Opinion dated Oct. 18, 2012 for International Application No. PCT/US2012/034480.

International Search Report and Written Opinion dated Sep. 2, 2008 in PCT Application No. PCT/US2008/061043, filed Apr. 21, 2008.

Merriam-Webster.com definition of "tray"; http://www.merriam-webster.com/dictionary/tray.

Partial International Search Report dated Apr. 27, 2010 for International Application No. PCT/US2008/080832, filed Oct. 22, 2008.

Partial International Search Report dated Jul. 6, 2012 for International Application No. PCT/US2012/034480, filed Apr. 20, 2012.

Supplementary European Search Reported dated Dec. 10, 2010 for European Application No. 08746468.1, filed Apr. 21, 2008.

Extended European Search Report received in European Patent App. No. 08746468, dated Nov. 23, 2010.

International Preliminary Report on Patentability in PCT App. No. PCT/US2011/020415, dated Jan. 30, 2012.

(56) References Cited

OTHER PUBLICATIONS

International Preliminary Report on Patentability issued in PCT Application No. PCT/US2012/034480, dated Nov. 14, 2013.
International Search Report and Written Opinion in PCT App. No. PCT/US2008/061043, dated Aug. 27, 2008.
International Search Report and Written Opinion in PCT App. No. PCT/US2014/067717, dated Mar. 5, 2015.
Office Action, Korean Patent Application No. 10/2015-7020105, 5 pages, Aug. 27, 2015.
Office Action, European Patent Application No. 12187535.5, 4 pages, Aug. 14, 2015.
Search Report, European Patent Application No. 15152563.1, 5 pages, Jul. 23, 2015.
Office Action, Chinese Patent Application No. 201180011864.8, 9 pages, Oct. 28, 2015.
Japanese Office Action, Application No. 2015-108508; 8 pages with translation, Mar. 28, 2016.
Australian Office Action, Application No. 2015210377; 4 pages.

\* cited by examiner

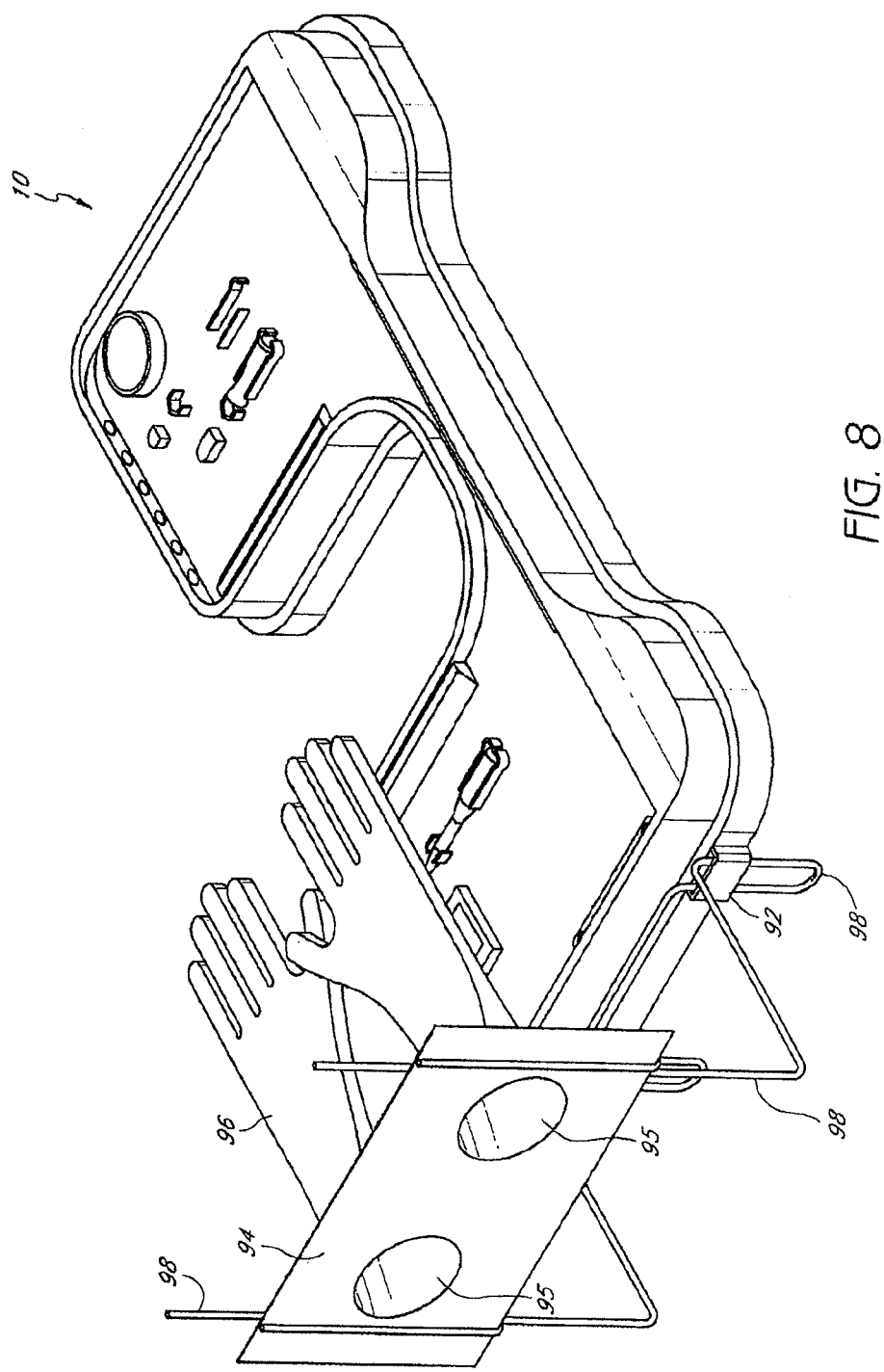

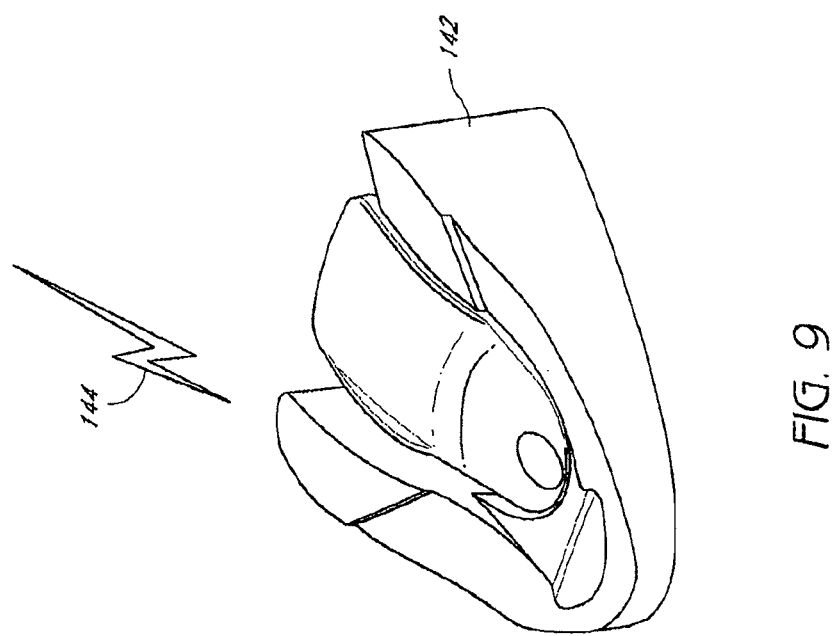

STERILE SURGICAL TRAY

CROSS REFERENCE TO RELATED APPLICATIONS

This application is a continuation of U.S. patent application Ser. No. 12/684,850, titled STERILE SURGICAL TRAY, filed Jan. 8, 2010, which is a continuation-in-part application of U.S. application Ser. No. 12/256,420 filed Oct. 22, 2008, and titled STERILE SURGICAL TRAY, which is a continuation-in-part application of U.S. application Ser. No. 12/107,038 filed Apr. 21, 2008 and titled INDEPENDENT SURGICAL CENTER, which claims the benefit of U.S. Provisional Application No. 60/925,546 filed Apr. 20, 2007, and titled INDEPENDENT SURGICAL CENTER INCLUDING A PORTABLE VITRECTOMY HANDPIECE AND INFUSION/ASPIRATION CASSETTE. U.S. application Ser. No. 12/256,420 is also a continuation-in-part application of U.S. application Ser. No. 12/107,052 filed Apr. 21, 2008, and titled PERSONAL SURGICAL CENTER, which claims the benefit of U.S. Provisional Application No. 60/925,562 filed Apr. 20, 2007, and titled PERSONAL SURGICAL CENTER. U.S. application Ser. No. 12/256,420 is also a continuation-in-part application of U.S. application Ser. No. 12/106,962 filed Apr. 21, 2008, and titled SURGICAL PACK AND TRAY, which claims the benefit of U.S. Provisional Application No. 60/925,548 filed Apr. 20, 2007, and titled SURGICAL PACK AND TRAY.

U.S. patent application Ser. No. 12/684,850 is also a continuation-in-part application of U.S. application Ser. No. 12/107,038 filed Apr. 21, 2008, and titled INDEPENDENT SURGICAL CENTER, which claims the benefit of U.S. Provisional Application No. 60/925,546 filed Apr. 20, 2007, and titled INDEPENDENT SURGICAL CENTER INCLUDING A PORTABLE VITRECTOMY HANDPIECE AND INFUSION/ASPIRATION CASSETTE. U.S. patent application Ser. No. 12/684,850 is also a continuation-in-part application of U.S. application Ser. No. 12/107,052 filed Apr. 21, 2008, and titled PERSONAL SURGICAL CENTER, which claims the benefit of U.S. Provisional Application No. 60/925,562 filed Apr. 20, 2007, and titled PERSONAL SURGICAL CENTER. U.S. patent application Ser. No. 12/684,850 is also a continuation-in-part application of U.S. application Ser. No. 12/106,962 filed Apr. 21, 2008, and titled SURGICAL PACK AND TRAY, which claims the benefit of U.S. Provisional Application No. 60/925,548 filed Apr. 20, 2007, and titled SURGICAL PACK AND TRAY.

Each of the foregoing applications is hereby incorporated by reference in its entirety, specifically the systems, methods, and devices for relating to a surgical tray.

BACKGROUND

1. Field

The invention is related to a surgical tray that technology, and in particular to a sterile surgical tray that allows a surgeon or other user to directly monitor from the surgical tray and/or directly control from the surgical tray other tools and instruments associated with the surgical tray. The surgical tray can also function as both a pack to transport surgical materials and devices to a surgery site and as a sterile tray for receiving a plurality of surgical instruments. The sterile surgical tray can also include a plurality of electrical input and output connectors attached to the tray.

2. Description of the Related Art

It is well known to use, in surgery, a sterile pack shipped from a manufacturer to a surgery center, an example of which is ophthalmic surgery (vitreoretinal or cataract surgery, in particular). These packs typically contain several items that are typically used in surgery and include one-time use surgical instruments, fluid cassettes, tubing sets, drapes, needles, and other devices. The particular content of a pack depends on the type of surgery and perhaps the individual preference of the surgeon or surgery center.

When preparing for surgery, typically a sterile drape is placed over what is commonly referred to as a Mayo tray. The contents of the sterile pack and perhaps additional sterile instruments and materials are spread-out over the tray so that the materials and instruments necessary for the surgery are readily available to a nurse or surgeon.

It is also known to provide a sterile pack where many of the instruments and tubing sets are organized and placed in mating recesses of the pack so that the pack can act as a tray for at least some of the instruments in surgery.

Some of the surgical instruments are electrically or pneumatically powered by a surgical console or system that is outside of the sterile field defined by the surgical site and the sterile instruments and materials on the tray and used in the surgery. Some of the sterile materials are removed from the sterile field or a portion is removed from the sterile field prior to surgery. The materials removed include the pump cartridges and tubing sets which are connected to the non-sterile surgical console. The surgical console also typically includes a large display screen for displaying and inputting parameters that will control the devices used during surgery. This surgical set-up typically requires a surgeon and one or two support persons so that surgery can be performed efficiently while also adjusting the parameters on the console and switching to a different surgical instrument to perform a different procedure.

However, with the present trend of surgeries moving away from hospital and into ambulatory surgery centers (ASCs) and even into a doctor's own office, coupled with reduced reimbursements for surgical procedures, there is a need to allow surgeons to perform surgery with little or no assistance. In addition, because of personnel and cost restraints the assistant provided to the surgeon is typically not trained in the particular surgical procedure to be performed, so that the interaction between the surgeon and assistant may not be particularly efficient.

Therefore, a need exists for a surgical system and surgical products that allow a surgeon to perform safe, efficient, and cost-effective surgery with little or no assistance during surgery.

SUMMARY

In certain embodiments, a sterile surgical tray comprises a sterile tray, a pump within the sterile tray, and a motor within the sterile tray connected to the pump. Desirably, the tray includes structure for receiving a plurality of surgical instruments. It is also desirable that the tray contain at least one pump fluid reservoir and that the reservoir be operatively connected to the pump. In a distinct embodiment, a sterile surgical tray comprises a plurality of electrical input and output connectors attached to the tray.

In certain embodiments, an infusion fluid reservoir comprises a multiple chamber fluid reservoir for holding a different fluid in each chamber; a pressure pump connected to two or more chambers for pressurizing the chambers; and a multiple position valve connected to the multiple chambers for selectively opening one of the multiple chambers to allow a fluid contained in a selected chamber to flow out of the selected chamber.

In certain embodiments, a sterile surgical tray comprises a receiving area for holding a plurality of surgical instruments; a fluid reservoir disposed apart from the receiving area; a pump operatively connected to the fluid reservoir; a motor drivingly coupled to the pump; and a plurality of input and output connectors attached to the sterile tray, at least one of the input and output connectors being connected to the motor. A sterile surgical tray system can comprise in certain embodiments a tray with a top surface defining a sterile surface for holding a plurality of surgical instruments; at least one surgical instrument held on the top surface; a pump fluid reservoir for use with the at least one surgical instrument; a pump operatively connected to the at least one surgical instrument and to the pump fluid reservoir; a motor connected to the pump for driving the pump; and wherein at least the pump remains within a sterile field during surgery.

In certain embodiments, a sterile surgical tray comprises a top surface for holding a plurality of surgical instruments; a pump connected to the sterile tray and for connection to a fluid pump reservoir; and a motor connected to the pump for powering the pump. A sterile surgical tray can comprise in certain embodiments a tray having a sterile top surface for holding a plurality of surgical instruments; a pump fluid reservoir prepackaged and sterilized with the tray; a pump in the tray for operative connection to at least one surgical instrument and the pump fluid reservoir; and a motor connected to the pump for powering the pump.

In certain embodiments, an independent system for a surgical procedure comprises a control device including a processing unit; and a plurality of instruments associated with the surgical procedure and operably coupled to the control device, wherein the control device and the plurality of instruments are prepackaged together, and the processing unit is configured to control at least one of the prepackaged instruments. In certain embodiments, at least one of the plurality of electrical instruments comprises a processing unit. The processing unit can be configured to establish communication between each of the plurality of electrical instruments. In certain embodiments, the communication can be wireless communications. In certain embodiments, the processing unit can be configured to: receive status updates from the plurality of electrical instruments; and communicate with status updates to a user of the system.

In certain embodiments, a surgical system comprises a portable surgical tray including a processing unit; a plurality of instruments operably coupled to the processing unit; and a user input device providing a user input for controlling an operating parameter of one or more of the plurality of instruments, wherein the processing unit is configured to receive the user input and transmit an operating command to the one or more of the of the plurality of instruments. In certain embodiments, the processing unit is further configured to receive and/or monitor operating parameters from the plurality of instruments. In certain embodiments, the processing unit is further configured to transmit a shut down command to a handpiece in the event that at least one operating parameter meets a threshold, for example, as a safety mechanism.

In certain embodiments, a self-powered surgical system for a surgical procedure, comprises a surgical tray; a plurality of handheld instruments; a power source in at least one of the surgical tray and a handheld instrument; and a processing unit; wherein the processing unit is configured to execute program instructions, the program instructions including instructions for: detecting power from the at least one power source; directing power to the plurality of handheld instruments from the at least one power source; and establishing communication with each of the plurality of handheld instruments.

In certain embodiments, a portable biological cutting and aspiration device comprises a cutting tip; a fluid aspiration device; and an integrated control unit coupled to the cutting tip and fluid aspiration device, wherein the control unit is configured to control cutting and aspiration of the cutting tip and fluid aspiration device.

In certain embodiments, a surgical system comprises a portable surgical platform configured to perform at least one of cutting, resecting, illuminating, lasering, aspirating, infusing, cauterizing, cryopreserving biological tissue and fluids, and infusing and aspirating fluids in a human body during surgical procedures, wherein the surgical platform is at least in part disposable; and a monitoring center coupled to the surgical platform for monitoring one or more operating parameters during the surgical procedures.

In certain embodiments a personal surgical center comprising a portable computer unit in wireless communication with at least one of a plurality of handheld instruments, the portable computer unit including a processor and memory having program instructions stored therein, the processor being operable to execute the program instructions, the program instructions including: automatically identifying at least one of the plurality of handheld instruments; wirelessly receiving operation status of the identified handheld instruments; monitoring changes in the operation status of the identified handheld instruments; and displaying the operation status on a display.

In certain embodiments, a surgical system comprises a control system accessible by a surgeon for controlling operational parameters of a one or more medical instruments; a monitoring system including a general purpose computer in wireless communication with the control system, the general purpose computer including a processor and memory having program instructions stored therein, the processor being operable to execute the program instructions, the program instructions including: wirelessly identifying the medical instruments controlled by the control system; wirelessly receiving the operational parameters of the one or more medical instruments from the control system; monitoring changes in the operational parameters of the one or more medical instruments; and displaying the operational parameters of the one or more medical instruments on a display coupled to the general purpose computer.

In certain embodiments, a sterile surgical tray system comprises a sterile surgical tray for positioning in a surgical field, the sterile surgical tray further comprising at least one controller; and a rack system positioned apart from the sterile surgical tray and outside the surgical field, the rack system being in communication with the at least one controller of the sterile surgical tray.

In certain embodiments, a sterile surgical tray system comprises a sterile surgical tray for positioning in a surgical field, the sterile surgical tray further comprising at least one display; and a rack system positioned apart from the sterile surgical tray and outside the surgical field, the rack system being in communication with the at least one display of the sterile surgical tray.

In certain embodiments, a computer-implemented method for controlling a surgical system, the method comprises receiving user input at a controller coupled to a sterile surgical tray in a surgical field; transmitting the user input to a rack system positioned apart from the sterile surgical tray and outside the surgical field; processing, using a processor in the rack system, to process the user input; and controlling a surgical apparatus based on the processed user input. In certain embodiments, the sterile surgical tray comprises the controller. In certain embodiments, a surgical device comprises the controller, wherein the surgical device is coupled to the sterile surgical tray or to the rack system. In certain embodiments, the surgical device is a handheld device, for example, a cutter device. In certain embodiments, the transmitting is performed through a wireless or wired connection to the rack system. In certain embodiments, the transmitting is performed through a wireless or wired connection to the sterile surgical tray, which is in electronic communication with the rack system. The surgical apparatus can include without limitation a handheld surgical device (for example a cutter device), a vacuum control apparatus or vacuum source, a fluid control apparatus or fluid source, a light control apparatus or light source, an energy control apparatus or energy source (for example, electrical energy), or the like.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the present inventions are described in detail below with reference to the drawings of preferred embodiments, which are intended to illustrate and not to limit the invention. The drawings comprise several figures in which:

FIG. 8 is a perspective view of yet another embodiment of a sterile surgical tray in accordance with a preferred embodiment of the invention;

FIG. 9 is a perspective view of a foot controller to be used with a sterile surgical tray in accordance with a preferred embodiment of the invention;

DETAILED DESCRIPTION OF A PREFERRED EMBODIMENTS

Figure 1:
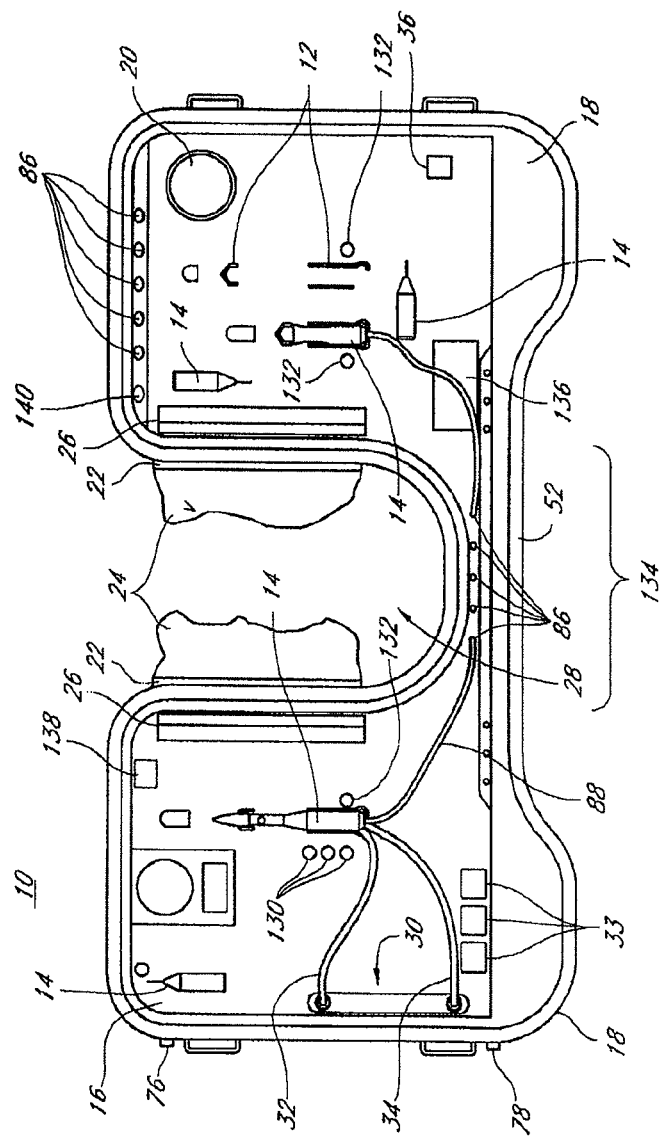
FIG. 1 is a top view of a sterile surgical tray in accordance with a preferred embodiment of the invention.

The following description will be disclosed relative to ophthalmic surgery but this is only for illustrative purposes and those skilled in the art will appreciate that the embodiments as described herein and as claimed may equally apply to other types of surgery, for example but not limited to ortho surgery, neurosurgery, cardiovascular surgery, gastrointestinal surgery, plastic and dermatological surgery, general surgery, head and neck surgery, including without limitation to ear, nose, and throat, maxilofacial surgery, vascular surgery, thoracic surgery (lung), transplant surgery, or the like.

Enabling a surgeon to perform effective surgery with minimal assistance from another and to perform surgery in a surgery center or office setting without a large capital investment, requires control of the surgical instruments and devices to be in the sterile surgical field. The sterile field is typically defined by the area adjacent the surgical site that is covered by a sterile drape and the area where the surgical instruments and materials are placed for access by the surgeon during surgery. The area where the surgical instruments are placed for surgery is typically a non-sterile tray, commonly referred to as a Mayo tray, covered by a sterile drape.

The embodiments of the invention described herein provide the surgeon with sterile field control of the surgery by providing the surgeon with a sterile surgical tray that has been manufactured and assembled as a prepackaged sterile pack that functions as a tray during surgery. The term pack is meant to collectively identify the surgical instruments and other items contained in a sterile package that is shipped from the manufacturer to a customer (hospital, ASC, doctor's office) and is for use by a surgeon to perform surgery. The term tray refers to a structure that defines at least a portion of a surgical field and holds fluid handling devices, surgical instruments, and other miscellaneous items to be used during surgery.

In a preferred embodiment, the pack can be synonymous with the tray. As will be seen below, in a preferred embodiment the inventive surgical tray may be manufactured and assembled with the necessary equipment for surgery and then enclosed in a bag or other container and sterilized. Then when the bag is opened, the tray is removed from the bag, a lid or cover is potentially removed, revealing several if not all the instruments and other items needed for surgery. Of course, variations on the preferred embodiment may be made without departing from the scope and claims. For example, while it is contemplated that the preferred sterile tray can be packaged and sterilized with a pump reservoir, pump, and motor, it may be that the reservoir, pump, or motor can be packaged without being sterilized. For example if the motor were contained in a chamber that was sealed off from the tray the motor may not need to be sterilized. As used herein, the term "motor" means and includes without limitation a device that receives and modifies energy to drive at least the pump.

A sterile surgical tray 10 is shown in FIG. 1. The tray 10 includes structure 12 for receiving a plurality of surgical instruments 14. The structure 12 for receiving the instruments 14 may be a mating structure, such as shown, that generally conforms to the shape of a particular instrument. As used herein the term "mating" means without limitation a receptacle having a complementary shape for recessing part or all of an article. Alternatively, the structure 12 could be a recess (not shown) in the tray 10 having a shape that may hold a variety of instruments 14 or the structure 12 may be cavities (not shown) formed in tray 10 that retain instruments 14 in a generally vertical orientation relative to top surface 16, or even some other suitable structure 12 may be used. The tray 10 should have sufficient area on top surface 16 to receive the surgical instruments 14 necessary for the surgery to be performed with sufficient space between the instruments 14 to allow the surgeon to easily and conveniently pick-up an instrument and return it to the tray 10.

The sterile tray 10 may be molded of such materials as acrylonitrile butadiene styrene (ABS) or similar thermoplastic material. The tray 10 may take the place of the traditional Mayo tray and may be placed between the surgeon and the surgical site. Therefore, it is preferred that tray 10 be sturdy enough to withstand the weight of a surgeon's arms resting on the structure forming arm rests 18. However, other accommodation may be made for a surgeon's arms and tray 10, in which case, tray 10 need not be as robustly constructed.

Tray 10 also may include structure forming a priming fluid reservoir 20 for receiving one or more instruments 14 during priming of one or more instruments with a surgical fluid such as balanced-salt solution (BSS), as is well known. If a reservoir 20 is not provided the user may need to use a beaker or other container for priming (for example, filling) the surgical instruments and tubes with BSS.

Structure 22 for attaching a drape 24 to the tray 10 may also be provided. The drape 24 may be placed over a patient, such as a portion of a patient's head (not shown) during ophthalmic surgery. Structure 22 may be any suitable structure such as adhesive tape, hook and loop material, or other structure that will attach drape 24 to tray 10. Using drape 24 allows for the use of at least one fluid retention trough 26 to collect fluid runoff from the drape 24 that occurs during surgery. FIG. 1 shows two troughs 26, but a single trough (not shown) could also be formed that surrounds the entire center section 28 where a patient's head (not shown) will be placed during surgery.

The surgical instruments 14 may include a plurality of instruments, and in particular ophthalmic surgical instruments prepackaged and sterilized with the tray 10. Also, at least one surgical instrument 14 may be connected at manufacture to a pump fluid reservoir 30 via tubing 32 and/or 34, as shown in FIG. 1. If the sterile surgical tray 10 is for ophthalmic surgery the plurality of surgical instruments 14 preferably includes at least a tissue isolation instrument, an aspiration instrument, and an infusion instrument. The tissue isolation instrument may be at least one of a vitreous cutter, a lens emulsification, fragmentation, or cutting device, a scissors, and a cautery knife, all of which are well known. The aspiration instrument may be incorporated into the tissue isolation instrument, such as is known in vitreous cutters and phacoemulsification (phaco) devices. The aspiration and infusion instruments may be a combined infusion and aspiration instrument, commonly referred to as an irrigation/aspiration (I/A) handpiece. If the surgical tray 10 is for vitreoretinal surgery the infusion instrument may be an infusion cannula and connected tubing.

Additional surgical instruments may include an illumination instrument, which is preferably self-illuminating. That is the illumination instrument preferably has a built-in light source and not the commonly known remote light source-fiber optic combination. In addition tray 10 may include additional items such as entry site alignment cannulas 36, commonly used in sutureless vitreoretinal surgery.

Preferably tray 10 includes all or nearly all the instruments necessary to perform the desired surgery. For instance tray 10, if the desired surgery is a vitrectomy of the eye, includes the instruments for a vitrectomy, which are a vitreous cutter, an irrigation instrument, an illumination instrument, an aspiration source, an infusion source, and passive surgical instruments (for example, not powered), and possibly an air/fluid exchange source. If the desired surgery is a cataract removal from the eye, the instruments included in tray 10 would be a cataract extraction instruments such as a phaco device, a phaco needle, a capsule polish tool, an aspiration source, an infusion source, and passive surgical instruments, and possibly an oil filled syringe. Tray 10 also preferably includes structure for receiving additional instruments beyond the plurality of instruments that are prepackaged and sterilized with the tray 10; an example of which is the empty space, shown generally at 38 in FIG. 1.

Figure 2:
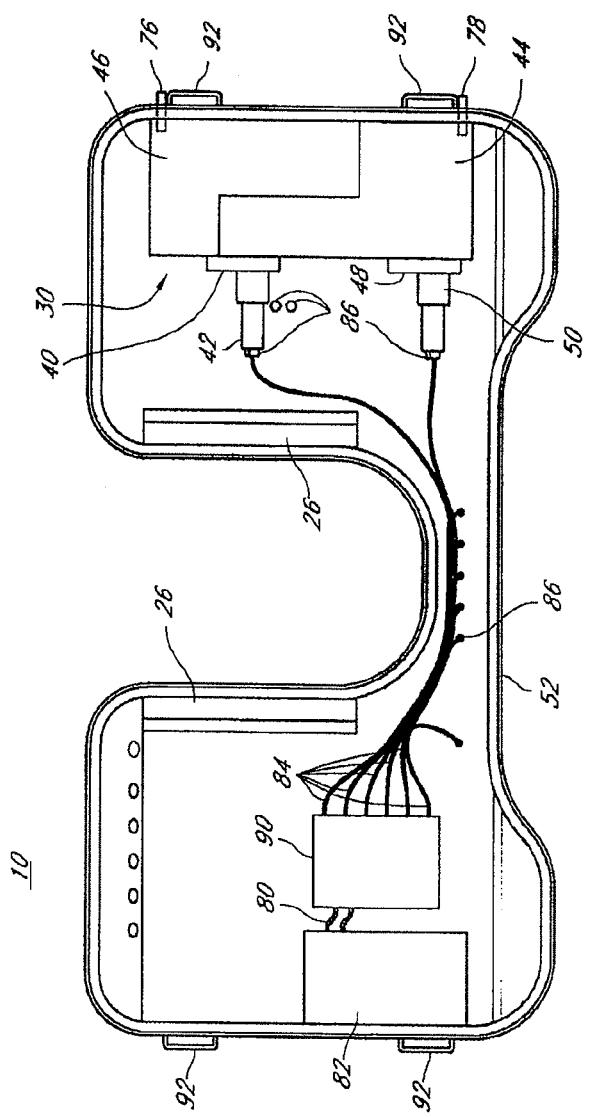
FIG. 2 is a bottom view of the tray of FIG. 1.

In certain embodiments, the sterile surgical tray 10, as best seen in FIG. 2, also includes a pump(s) 40 contained within the sterile tray 10 operatively connected to the pump fluid reservoir 30. In certain embodiments, a motor(s) 42 is also contained within the sterile tray 10 and is connected to the pump 40. In certain embodiments, the sterile surgical tray 10 can be configured to releasably receive a motor(s) and a pump(s), and/or be mechanically and/or electrically coupled to a motor(s) and a pump(s), which may or may not be partially or entirely sterile because in certain embodiments, the motor(s) and/or pump(s) may be reused with other sterile surgical trays. In the embodiment shown in FIG. 2, which is a bottom view of tray 10, reservoir 30 is not easily removable from tray 10. Other embodiments (see for example FIG. 6 discussion below) may provide a reservoir, pump, motor assembly that is self-contained and placed in a pocket or cavity (not shown) of tray 10 so that the assembly can be removed from tray 10 easily before, during, or after surgery.

Reservoir 30 may be an aspiration pump fluid reservoir for collecting aspirated tissue and fluid during surgery or reservoir 30 may be infusion pump fluid reservoir for infusing fluid into a surgical site. Another embodiment of reservoir 30 is that shown in FIG. 2 where reservoir 30 is actually both an aspiration reservoir 44 and an infusion pump fluid reservoir 46; such that infusion reservoir 46 and aspiration reservoir 44 form a single fluid reservoir 30 with separate chambers for infusion and aspiration and a pump operatively connected to each chamber. Therefore, in the configuration of FIG. 2 pump 40 is an infusion pump and pump 48 is an aspiration pump. Motors 42 and 50 are preferably electric motors and may be the same type motor or different motors depending on the performance needed to drive the pumps 40 and 48. Aspiration pump 48 is preferably a suitable pump for aspirating a sufficient amount of tissue and fluid at an acceptable rate for the type of surgery to be performed. For ophthalmic surgery, pumps 40 and 48 may be one of a vacuum pump (for example, a rotary vein or diaphragm) or a positive displacement pump (for example, peristaltic or scroll). Tray 10 may also include a syringe pump (not shown) for injecting oil or other fluids into the eye.

In certain embodiments, the inclusion of a pump and reservoir in tray 10 provides particular fluidics advantages over traditional console based systems. For example, fluidics advantages can be achieved because the construction and functionality of tray 10 allow the pump fluid reservoir to be less than two feet from a surgical site, such as an eye. This close proximity can allow for infusion and aspiration tubing lengths of less than two feet and perhaps less than 18 inches to be used. By using such short tubing lengths compliance of the fluidics circuit defined by the path from the infusion reservoir 46 through infusion tubing and a surgical instrument into the eye followed by an aspiration out of the eye through aspiration tubing and into the aspiration reservoir 44, can be greatly reduced compared to the conventional console based surgeries known today. Conventional console based surgeries use several feet (as much as 6-8 feet) of tubing for both the infusion path and the aspiration path. Furthermore, a reduced aspiration and infusion tubing length reduces fluid propagation delays and increases responsiveness of the aspiration and infusion functions. The 6-8 feet tubing length can negatively impact fluidic performance as compared to the much shorter tubing lengths possible in the preferred embodiments. The longer tubing lengths have longer delays in pressure and vacuum level changes introduced into the surgical instruments and an eye compared to the much shorter lengths of the preferred embodiments. These longer delays are the result of the increase tubing length and the compliance of the tubing. The effect of any tubing compliance will be amplified by longer tubing lengths. The shorter tubing lengths can also reduce the complexity of the surgical operation for the surgeon because with multiple lengthy tubes in the surgical room the surgeon generally must take care not to entangle the lengthy tubes or to pinch the lengthy tubes during the surgery.

Figure 3:
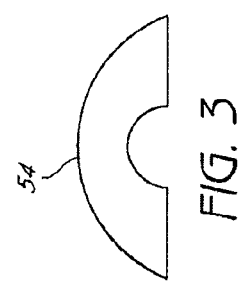
FIG. 3 is a view of an alternate shape of a sterile surgical tray in accordance with a preferred embodiment of the invention.

Tray 10 may have a shape that conforms to a contour of a body portion adjacent a surgical site. As can be seen from FIGS. 1 and 2 tray 10 is curved so that the tray 10 may be placed around a patient's head (not shown) during ophthalmic surgery. Tray 10, which can be said to be generally U-shaped, would be placed such that a top of the patient's head is placed nearest the wall 52 or, put another way, at the bottom of the U-shaped section 28. The sterile surgical tray for ophthalmic surgery may also be semi-circular in shape, as shown at 54 in FIG. 3. Fluid reservoir 30 is preferably located to a side of the patient's head during surgery, as shown in the embodiment of FIGS. 1 and 2.

Figure 5:
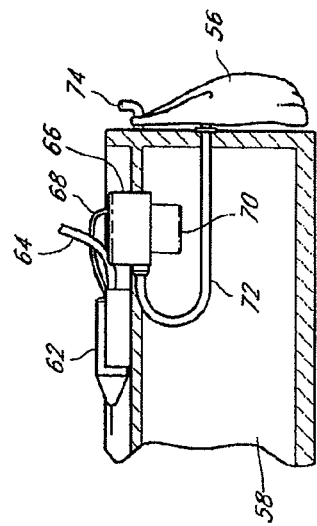
FIG. 5 is a partial elevation view of FIG. 4.
Figure 4:
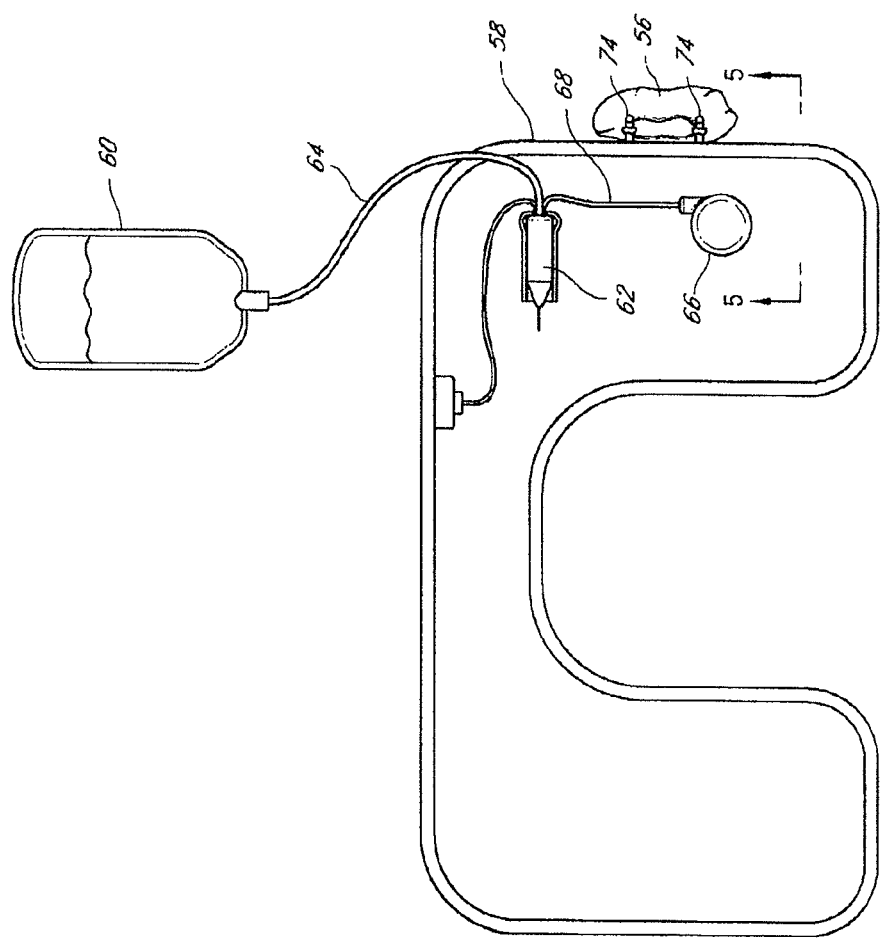
FIG. 4 is a top view of an alternate embodiment of a sterile surgical tray in accordance with a preferred embodiment of the invention.

Fluid reservoir 30 may be a rigid housing formed of suitable material such as some form of plastic or resin. The Pump fluid reservoir may also be a bag 56, shown in FIG. 4. A sterile surgical tray 58 similar to tray 10, in the embodiment of FIG. 4, includes a remotely located infusion source 60, such as a BSS bottle that may be hung from an IV pole (not shown). Infusion source 60 is connected to a surgical instrument 62 via tubing 64 (preferably included in tray 58 during manufacture). Instrument 62 is connected to a pump 66 via tubing 68. Pump 66 is powered by a motor 70, seen in FIG. 5. FIG. 5 is a partial elevation view of the inside of tray 58 taken along line 5-5 of FIG. 4. Pump 66 aspirates tissue and fluid from a surgical site into bag 56 via tubing 72. Bag 56 may be hung from structure on tray 58 such as hooks 74.

In reference to FIGS. 1 and 2, fluid reservoir 30 preferably includes a filler port 76 for allowing a user to fill the fluid reservoir 46 with a surgical fluid to be infused into a surgical site. Fluid reservoir 44 preferably includes a discharge port for emptying aspirated fluid when the reservoir 44 becomes full during surgery.

Figure 6:
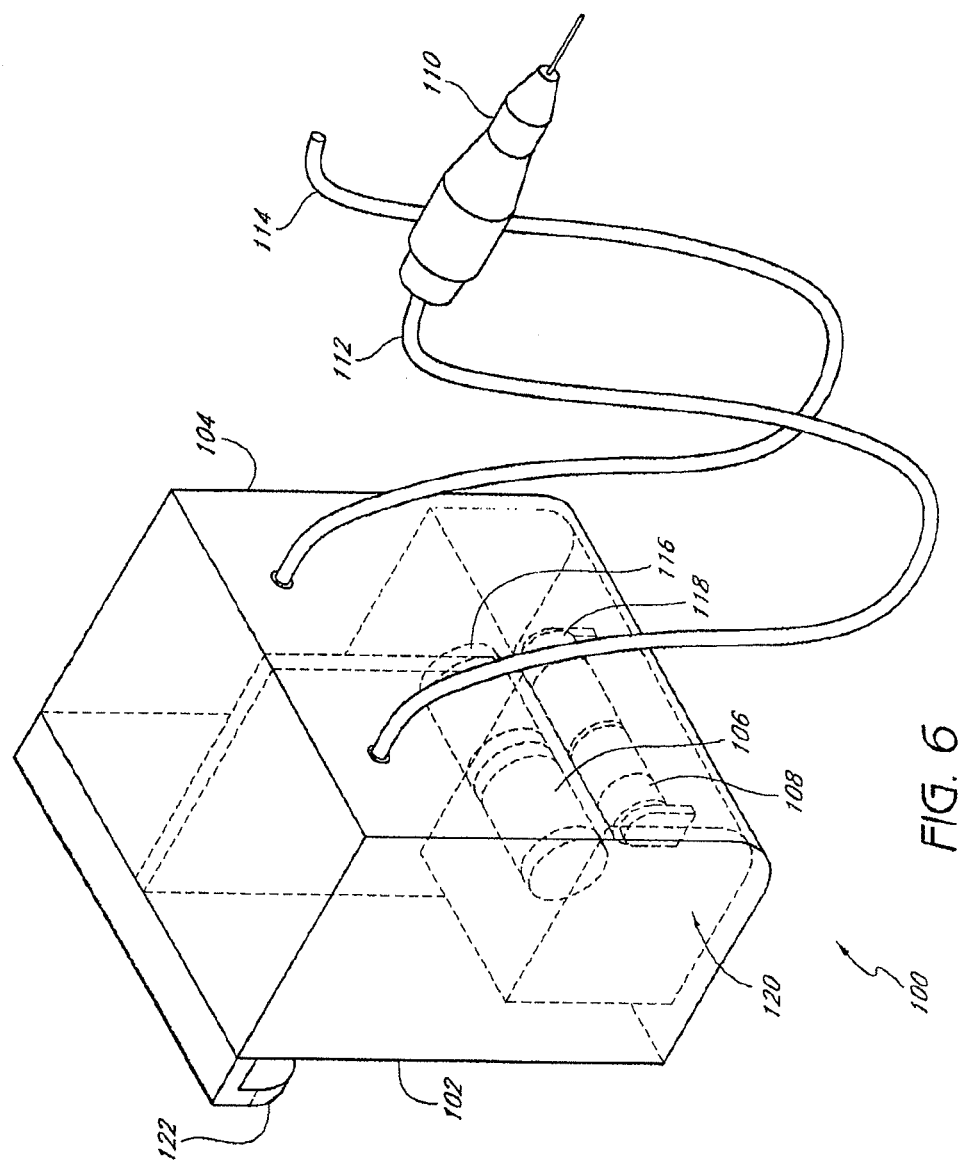
FIG. 6 is an alternate embodiment of a portion of a sterile surgical tray in accordance with a preferred embodiment of the invention.

FIG. 6 shows an aspiration and infusion reservoir 100, including isolated aspiration reservoir 102 and infusion reservoir 104. Reservoir 100 includes a separate pump and motor for each chamber 102 and 104. An aspiration pump 106 and motor 108 will aspirate fluid and tissue from a surgical site through surgical instrument 110 via tubing 112. Infusion fluid contained within infusion reservoir 104 is forced from reservoir 104 through tubing 114 to an infusion instrument (not shown) by infusion pump 116 and motor 118 pressurizing reservoir 104. An example of an infusion instrument can be an infusion cannula that is inserted into the eye to allow infusion fluid to enter the eye and maintain internal eye pressure to prevent collapse of the eye. As can be seen pumps and motors 106, 108, 116, and 118 are contained within a chamber 120 of reservoir 100. It is possible that because of the isolation of the pumps and motors in chamber 120 that they may not need to be sterilized along with reservoir 100 and its associated tray and surgical instruments after packaging at a manufacturer. It is accepted protocol that any surface that comes in direct contact with the infused or aspirated fluids should be sterile. Though an associated tray is not shown with reservoir 100 it is easily understood that reservoir 100 could be retained in and prepackaged and sterilized with a tray in a similar fashion to that described above relative to tray 10. In addition, it is possible that reservoir 100 may be removed from a tray and placed or hung by ledge 122 at a convenient location for surgery.

Figure 7:
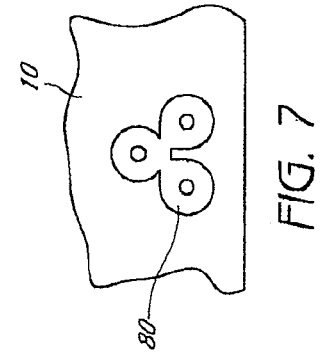
FIG. 7 is a partial view of another embodiment of a sterile surgical tray in accordance with a preferred embodiment of the invention.

Tray 10 further includes a power connector 80 connected to motors 42 and 50 for connecting motors 42 and 50 to a power source 82 via lines 84. Power source 82 is shown in FIG. 2 as a battery but the power source could be at least one of a direct current (DC) source, an alternating current (AC) source, a fuel cell, or a wireless power source, such as Witricity, or some other suitable power source. So power connector 80 can be at least one of an AC connector, a fuel cell connector or a wireless power connector instead of the battery connector shown. FIG. 2 shows one power source connection but it is to be understood that multiple power sources may be used. In addition, power source 82 may not be prepackaged and sterilized with tray 10 as shown, but rather, may be a power source that is connected to tray 10 after tray 10 is opened and is being prepared for surgery. Power connector or connectors 80 may be attached to a portion of tray 10, such as in a side wall of tray 10, as shown in FIG. 7; where power connector 80 is for connection to a DC source, an AC source, or an AC cord (not shown) to be plugged into a wall socket (not shown). If wireless power transmission is used it is possible that lines 84 can be eliminated if the surgical instruments are able to incorporate the power transmission apparatus. Obviously not all surgical instruments need power and some instruments may be self-powered by battery or fuel cell.

In the case where a power source is connected after tray 10 is opened, it may not be necessary for the power source to be sterile. For instance, the lower portion of tray 10 may have an opening for accepting a battery pack or fuel cell. In this case a non-sterile battery pack or fuel cell could potentially be used because it is below the sterile field top surface 16 of tray 10.

Power connector 80 may be connected directly to motors 42 and 50 and at least one surgical instrument 14 such that power source 82 powers the pumps and at least one surgical instrument 14, as shown in FIG. 2. At least one surgical instrument 14 is connected to power connector 80 through one of lines 84, an input and output connector 86, and line 88 (shown in FIG. 1). Of course more than one surgical instrument 14 may also be connected to power connector 80 through other input and output connectors 86, though these are not shown. The surgical instruments that can be connected include a vitreous cutter, a lens emulsification, fragmentation, or cutting device, an illumination device, and a scissors. In addition, the surgical instruments 14 may be prepackaged and sterilized with tray 10 and connected to pump reservoir 30 and input and output connectors 86.

Though power connector 80 may be connected directly to motors and surgical instruments, a power distributor 90, shown in FIG. 2, may be desired for distributing power throughout the sterile tray 10 for powering a plurality of surgical instruments. Depending on the power source used and the instruments needed for surgery power distributor 90 may take on many forms, such as a voltage transformer, a DC-to-DC converter, and an AC-to-DC converter. In addition power distributor 90 may also include a processor for performing control functions to operate the surgical instruments, motors, and operator feedback or status indicators, in other words power distributor 90 may also be the central controller for the entire surgical operation to be performed.

Tray 10, because of the desire to enable a surgeon to perform surgery with little or no assistance, preferably includes structure for connecting a sterile barrier to tray 10, such as slots 92. A sterile barrier 94 is attached to tray 10 in FIG. 8. Sterile barrier 94 includes a pliable sheet 96 that has at least one pocket 95 formed in the sheet 96 for allowing a non-sterile user (not shown) outside a sterile field to manipulate items within the sterile field without compromising the sterile field. The sheet 96 is attached to supports 98 that are in turn held within slots 92 of tray 10. Pocket 95 is shown as two pockets in FIG. 8 that form gloves for a user. It should be easily understood, that pocket 95 may take on other forms than gloves. For example, pocket 95 could simply be a cavity without any structure forming finger openings.

Tray 10, in addition to having structure for receiving a plurality of surgical instruments, preferably includes a plurality of input and output connectors 86 attached to tray 10, as seen in FIGS. 1 and 2. So as best seen in FIG. 2, sterile surgical tray 10 preferably includes pump fluid reservoir 30 contained within sterile tray 10, a pump or pumps 40 and 48, and a motor or motors 42 and 50 connected to the pumps and at least one of the input and output connectors 86 is connected to the motors 42 and 50 for connecting the motors 42 and 50 to a power source 82, such as the battery shown.

Tray 10 further may include at least one status indicator 130 attached to at least one of the output connectors 86. The status indicator may be a light emitting diode (LED) or an audible signal generator. In FIG. 1, on the left side three status indicators 130 are shown adjacent a surgical instrument 14. Depending on the type of instrument 14 the three status indicators 130 could provide different types of feedback to a user. For example, if reservoir 30 included a sensor the indicators 130 could be red, yellow, and green in color to indicate to the user that a vacuum level is unacceptable (red), a vacuum level is approaching an unacceptable level (yellow), or the vacuum level is acceptable (green). Another example is that the indicators 130 could indicate a speed or energy level of the instrument where all three indicators are on when the speed or energy level is high, two indicators are on when the speed or energy level is at an intermediate level, and one indicator is on when the speed or energy level is low.

Because tray 10 is used in an operating room that may be dark for certain surgeries, such as ophthalmic surgery, it is desirable that a plurality of LEDs 132 are connected to a plurality of output connectors 86 and at least one LED 132 is connected to tray 10 adjacent each of a plurality of surgical instrument retaining recesses 12 for illuminating a location of the surgical retaining recesses 12 on the tray 10. Preferably, a plurality of surgical instruments 14 are retained in tray 10 and connected to a portion of the plurality of input and output connectors and prepackaged and sterilized with the tray.

Depending on the type of surgery for which tray 10 is intended it may be desirable for tray 10 to be sufficiently narrow at a location 134 that will be immediately between a patient and a surgeon to allow the surgeon unrestricted access to a surgical site. In the example of FIG. 1, location 134 is in the center of tray 10 and forms the bottom of the U-shape of tray 10. It also may be desirable where tray 10 includes a plurality of surgical instruments retained in tray 10 and connected to a portion of the plurality of input and output connectors 86, that the input and output connectors 86 connected to the plurality of surgical instruments are attached to tray 10 at a generally central location 134, so that the connected instruments may be placed on either side of the tray to accommodate either a left or right handed surgeon.

The status indicators 130, in a similar fashion to the discussion above, may also be placed on tray 10 to indicate a power level of a battery or fuel cell, a fluid level of a pump fluid reservoir attached to the input and output connectors or an illumination level of an illuminator attached to the input and output connectors. An alternative or supplement to the status indicators and LEDs 130 may be a display 136 for displaying, via numbers, icons, bar graphs, and the like, the status of the instruments and/or other apparatus connected to tray 10. As discussed above, tray 10 may also have a processor attached to the input and output connectors 86 for receiving inputs from a user and a plurality of surgical instruments 14 and devices attached to the input and output connectors 86 and for transmitting signals to a user and the plurality of surgical instruments 14 and devices. The processor may be part of power distributor 90 or it may be a separate device. The processor may also be prepackaged and sterilized with tray 10 or it may be connected to tray 10 after tray 10 is opened and is being prepared for surgery.

Tray 10 may also include a wireless transceiver 138 connected to the input and output connectors 86 for transmitting and receiving signals to and from remote devices and surgical instruments. Wireless transceiver 138 may be any acceptable type of wireless communication device such as an infrared or radio frequency transceiver. Known examples of radio transceivers include Bluetooth®, Zigbee®, Wifi or IEEE 802.11 transceivers, or other known wireless communication devices. The wireless transceiver 138 can be connected a processor connected to tray 10 and to a laptop computer (not shown) in the operating room or elsewhere for monitoring or controlling a surgical procedure through the information flowing throughout tray 10 and the input and output connectors 86. For the sake of clarity and simplicity only some of the wires or lines 84 and some of the input and output connectors 86 have been shown in the drawings but it should be understood that potentially the processor could be remotely located from tray 10, and the control, monitoring, feedback, and/or communication signals could flow wirelessly between the processor and tray 10 via wireless transceiver 138.

In addition to the devices disclosed above some of the input and output connectors 86 may be connected to user input buttons, knobs 33, or the like. Also, a foot control connector 140 may be attached to tray 10 for connecting a foot controller 142 shown in FIG. 9. Of course, foot controller 142 may also be connected to tray 10 via wireless transceiver 138 as indicated by symbol 144 in FIG. 9. It is also desirable that a portion of the input and output connectors 86 are for connection to additional instruments beyond the plurality of instruments prepackaged and sterilized in tray 10. For example, a surgeon performing vitreoretinal surgery may require a fragmentation instrument that is not included in prepackaged and sterilized tray 10 but it can be connected to tray 10 using a mating input and output connector 86.

Figure 10:
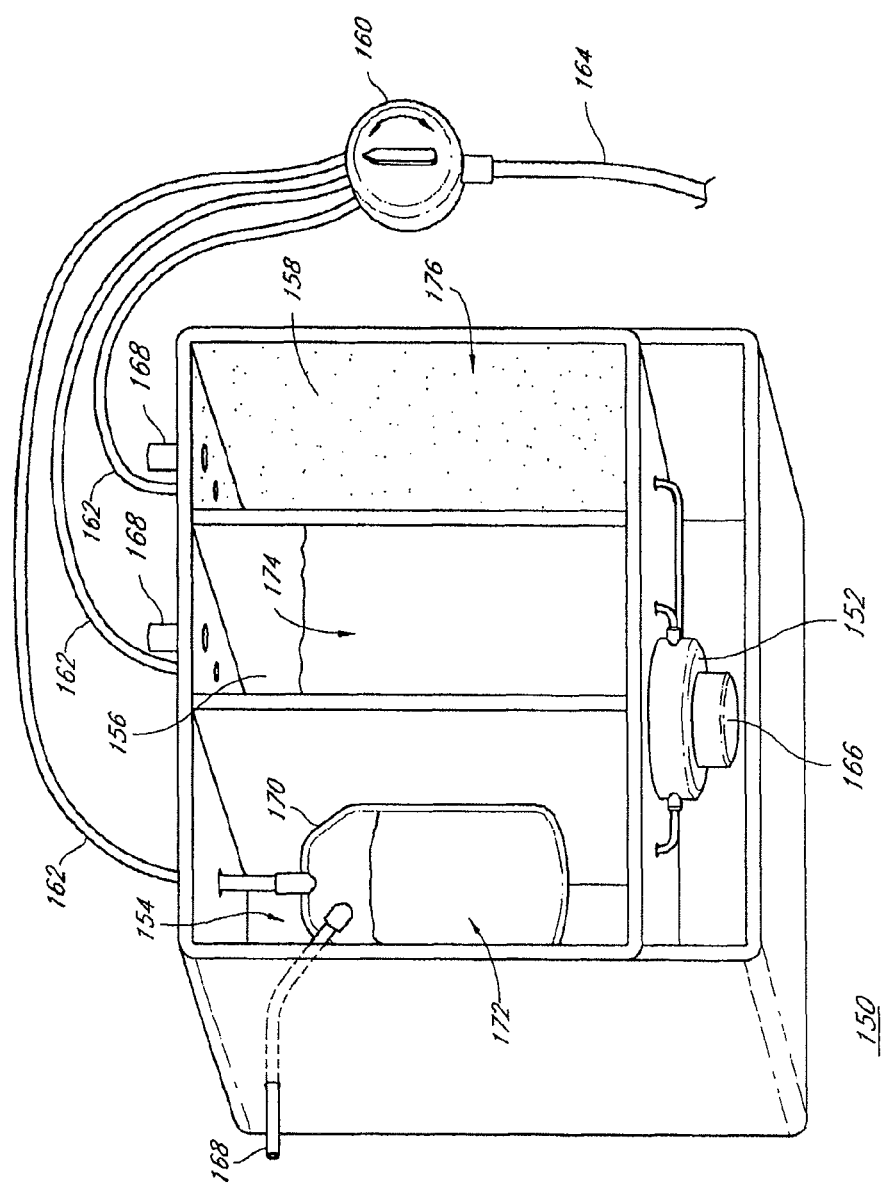
FIG. 10 is a perspective view of an alternate embodiment of an infusion fluid reservoir in accordance with a preferred embodiment of the invention.

Another example of an infusion fluid reservoir that may be used with a sterile surgical tray, is shown in FIG. 10. Infusion reservoir 150 is a multiple chamber fluid reservoir for holding a different fluid in each chamber. A pressure pump 152 is connected to two or more chambers 154, 156, and 158 for pressurizing the chambers. A multiple position valve 160 is connected to the multiple chambers 154, 156, and 158, via tubing 162. Valve 160 allows a fluid contained in a selected chamber to flow out of the selected chamber and into an eye or other surgical site through tubing 164 and a surgical instrument (not shown). Valve 160 is shown as a well known three position stop cock but valve 160 could also be individual valves or mechanically or electrically actuated valves depending on the design. If valve 160 is electrically actuated it could be attached or contained within tray 10 and connected to a portion of the input and output connectors 86 to support other than manual selection of the position of valve 160. The infusion fluid reservoir 150 shown has three chambers 154, 156, and 158, each chamber holding one of BSS, silicone oil, and a gas, which are particularly useful in ophthalmic surgery; but other fluids could be held in the chambers depending on the requirements of the particular surgery to be performed. For example, one of the chambers could contain viscoelastic. Infusion reservoir 150 is also preferably transparent so that a user can easily see the fluid levels in chambers 154, 156, and 158. It should also be appreciated that infusion fluid reservoir 150 has use beyond use with tray 10 and could be used with other surgical systems.

Infusion pump 152, powered by motor 166 pressurizes multiple chambers 154, 156, and 158 for infusing multiple fluids into a surgical site. It should be understood that motor 166 is connected to input and output connectors 86 (not shown) for power and control. Chambers 154, 156, and 158 also preferably include access ports 168 for filling or refilling the chambers. Ports 168 can require caps or closure devices to prevent fluids from leaking and to allow the chambers to be adequately pressurized. The chamber 154 shows a bag 170 partially filled with a fluid 172. Fluid 172 may be BSS or other liquid. Chamber 154 includes bag 170 at least partially filled with BSS such that pump 152 pressurizes the fluid reservoir chamber 154 during surgery to force BSS 172 from the fluid reservoir 150. Chamber 156 may hold silicone oil 174 and chamber 158 may hold a gas 176.

Figure 11:
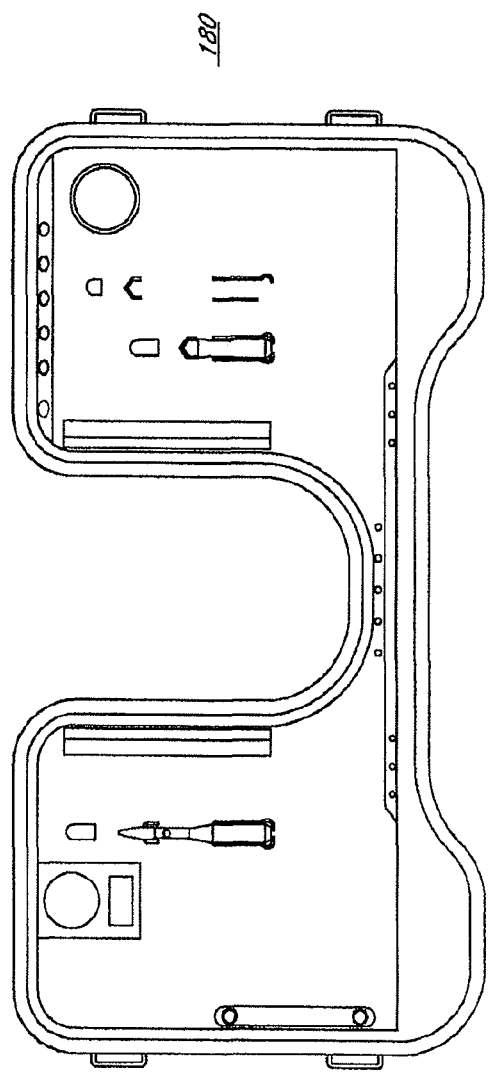
FIG. 11 is a top view of a sterile surgical tray for a specific surgery in accordance with a preferred embodiment of the invention.

FIG. 11 shows an example of a sterile surgical tray 180 including a plurality of surgical instruments including the instruments to perform a vitrectomy of an eye. To perform a vitrectomy at least an illumination instrument, a tissue cutting instrument, an infusion instrument, an entry site alignment system, and a surgical knife would typically be included in a sterilized tray such as tray 180.

Figure 12:
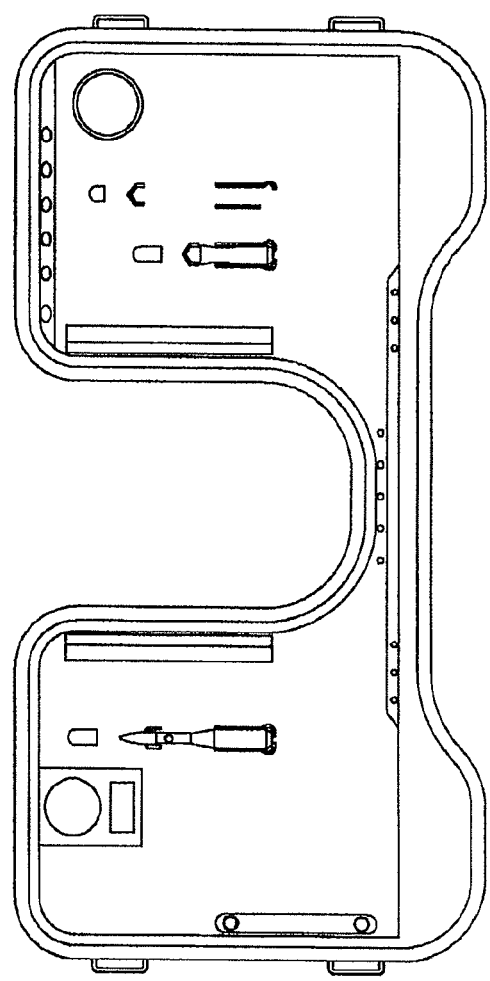
FIG. 12 is a top view of a sterile surgical tray for another specific surgery in accordance with a preferred embodiment of the invention.

FIG. 12 shows an example of a sterile surgical tray 182 including a plurality of surgical instruments including the instruments to perform a cataract removal from an eye. To perform a cataract removal at least a lens emulsification device, an infusion device, viscoelastic, a rhexis forceps, an intraocular lens insertion instrument, and a surgical knife would typically be included in a sterilized tray such as tray 182.

Figure 13:
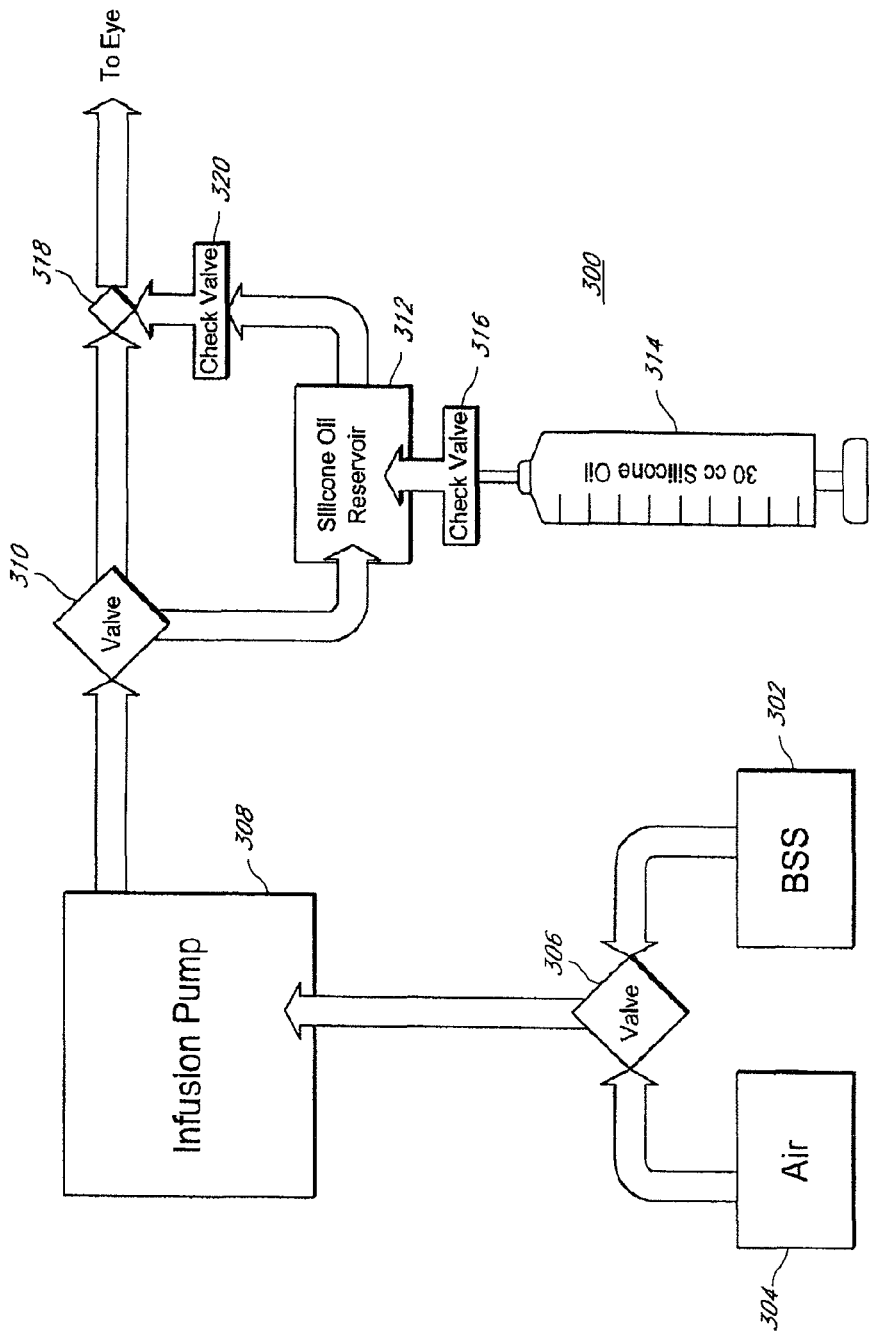
FIG. 13 is a functional block diagram of a fluid-air exchange system to be used with a sterile surgical tray in accordance with a preferred embodiment of the invention.

FIG. 13 is a functional block diagram of a fluid-air exchange system 300 is an alternative to pump reservoir 150 that may be incorporated into a sterile surgical tray, such as tray 10. System 300 preferably includes a BSS reservoir 302, a reservoir 304 of air, connected to a selector valve 306 for selecting which fluid, BSS or air, will be allowed to flow into infusion pump 308. Infusion pump 308 may be any suitable pump for infusing fluid into an eye or other body part. A bypass valve 310 connects a flow path from infusion pump 308 and an oil reservoir 312. Oil reservoir 312 is connected to a source of oil 314 via a check valve 316. Oil source 314 may be a syringe, as shown or may be another source that is connected to a pump (not shown) for automatically pumping oil into reservoir 312. Oil reservoir is then connected to a three-way stopcock valve 318 via another check valve 320. Depending on the positions of the valves 306, 310, and 318 air, BSS, or oil (typically silicone oil) will be infused into an eye. Bypass valve 310 allows infusion pump and air or BSS to push oil from reservoir 312 into an eye.

Figure 14:
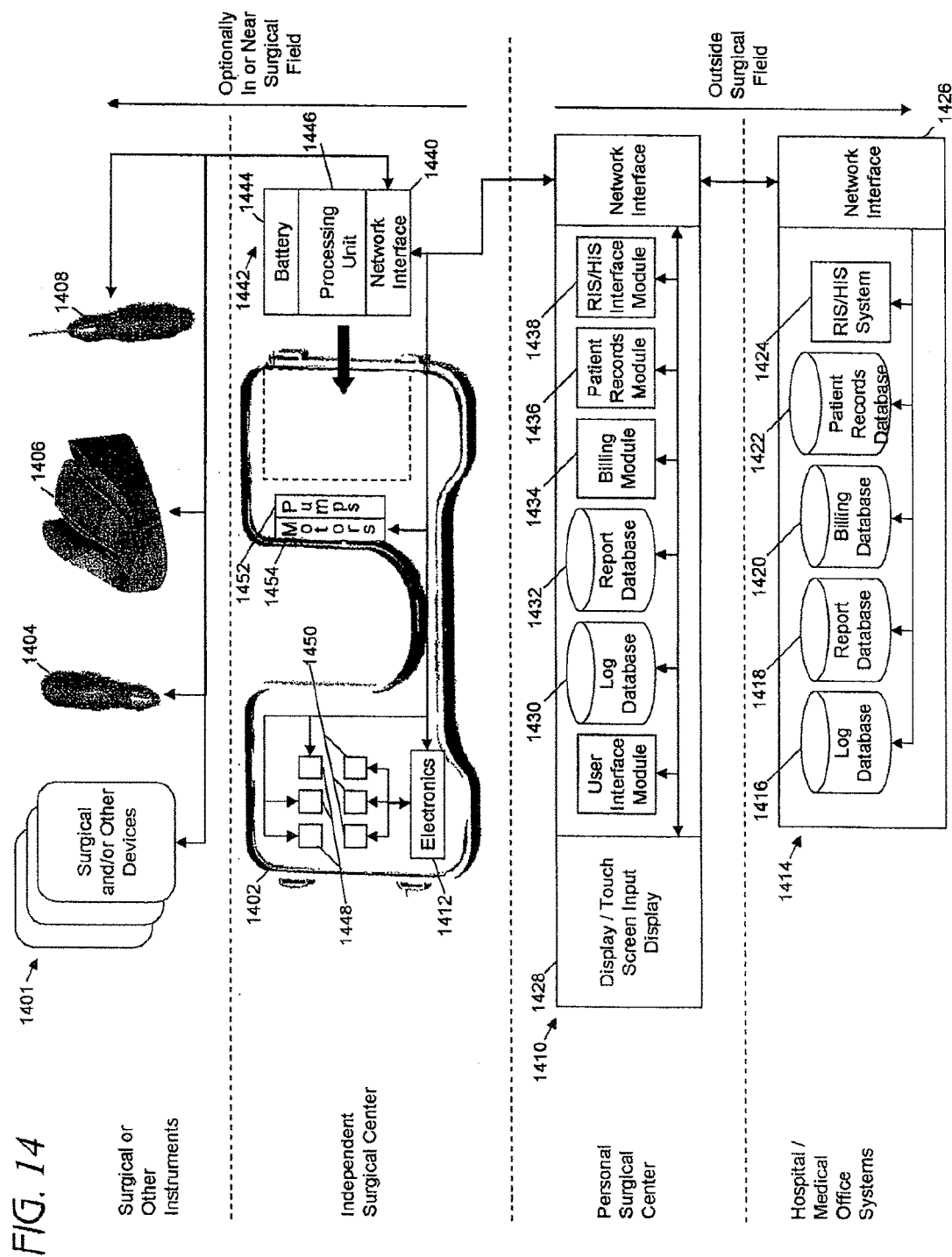
FIG. 14 is a block diagram illustrating an independent surgical center coupled to a personal surgical center, surgical or other instruments, and hospital and/or medical office systems in accordance with a preferred embodiment of the invention.

Independent Surgical Center and Personal Surgical Center in certain embodiments, the independent surgical tray 1402 can include at least the sterile surgical tray as described herein as illustrated in FIG. 14. The independent surgical center 1402 can be coupled to various surgical/medical or other devices 1401, a personal surgical center 1410, and/or a hospital/medical office system 1414.

In reference to FIG. 14, the independent surgical center can be operable without the use of an external surgical console, and can act as a standalone system. Alternatively, the independent surgical center can also be coupled to various surgical and/or other devices 1401 (also referred to herein as handpieces), for example but not limited to an illumination device 1407, foot pedal input device 1406, cutting device 1408 (also referred to as a biological tissue cutting device, as further described below), irrigation device, infusion device, viewing device, aspiration device, lasering device, cauterizing device, resecting device, lens emulsification device, fragmentation device, lens cutting device, scissor device, or any other like devices. In certain embodiments, the foregoing surgical and/or other devices can comprise a power source (internal or external, AC/DC), processing unit, network interface (wired or wireless), electronics, memory, audio mechanism, and the like. In certain embodiments, the independent surgical center 1402 communicates and/or is coupled/connected to the various surgical and/or other devices through a network interface 1440. The network interface 1440 can operate on a wired connection and/or a wireless connection using Bluetooth®, Zigbee®, Wifi or IEEE 802.11, or any other wireless communication protocol.

As illustrated in FIG. 14, the network interface 1440 can be coupled to a battery pack 1442, which can be received in, coupled to, and/or removed from the independent surgical center 1402. In certain embodiments, the battery pack 1442 comprises without limitation a battery or a plurality of batteries 1444, and a processing unit 1446. In certain embodiments, the processing unit can be in the independent surgical center 1402, the personal surgical center, a separate console, and/or the surgical devices, as described herein. The battery pack 1442 can comprise electrical contact and/or connectors for allowing the battery 1444, the processing unit 1446 (for example, Intel® 8085 microprocessor), and/or the network interface 1440 to be coupled and/or to connect to the circuitry and/or electronics 1412. In certain embodiments, the processing unit 1446 is configured to execute programming instructions stored in memory within the electronics 1412 to control light emitting diodes (LEDs) 1448, and/or receive user input through control knobs, buttons, or other input devices 1450. For example, the processing unit can be configured to control the LEDs to indicate/show the cutting device's status, speed, or other like indicators. The processing unit 1446 can also be configured to communicate with the motors 1452 coupled to the pumps 1454. The processing unit 1446 can also be configured to communicate and/or transmit commands to the surgical and/or other devices 1401 or to the personal surgical center 1410.

In reference to FIG. 14, the battery pack 1442 can be disposable or can be reused with other independent surgical centers 1402. The battery pack 1442 can be sterile or non-sterile, in which case the battery pack cannot be within the surgical field. In a preferred embodiment, the battery pack 1442 is reused with other independent surgical centers 1402 because of the cost of the batteries 1444, the processing unit 1446, and/or the network interface 1440, but in certain embodiments, the battery pack 1442 is disposable for purposes of sterility. The independent surgical center can also be coupled to a personal surgical center 1410.

With reference to FIG. 14, in certain embodiments, the personal surgical center 1410 can control the independent surgical center 1402. The personal surgical center 1410 can also include without limitation a console, general purpose computer, laptop computer, networked device(s), or the like that can be configured to monitor and/or display the settings of the various medical instruments (for example, the handpieces and/or surgical devices) on display or a touch screen input display 1428. Additional embodiments of the personal surgical center 1410 are described below. The personal surgical center 1410 can include without limitation a log database 1430 for storing real-time data and/or periodic data and status levels obtained and/or received from the independent surgical center. Based on the data, status levels, and/or patient information received from the independent surgical center and/or surgeon/technician, the personal surgical center 1410 can generate and/or store reports using the reports system and/or database 1432. The personal surgical center 1410 can also initiate billing procedures using the billing module 1434 that can interface with a billing system and database 1420. The personal surgical center 1410 can also store the data, status levels, and/or patient information in the patients records database 1422 using patient records module 1436, or can store this data in the hospital information system (HIS) 1424 using the HIS interface module 1438. In certain embodiments, the personal surgical center 1410 monitors and displays the settings and status of the various surgical and/or other devices while the independent surgical center controls the medical instruments via the circuitry and electronics 1412 in the independent surgical center, and the circuitry and controls in the various surgical and/or other devices. In certain embodiments, the personal surgical system 1410 can be coupled to other hospital/medical office systems 1414.

FIG. 14 also illustrates one embodiment of a hospital/medical office system 1414, which can include without limitations systems and databases 1416 for logging data from the personal surgical center 1410, systems and databases 1418 for generating reports, systems and databases 1420 for producing invoices, bills, and/or insurance claims, systems and databases 1422 for storing patient records, systems 1424 for interfacing with hospital information systems (HIS).

In reference to FIG. 14, in certain embodiments, the independent surgical center 1402 and surgical and/or other devices can be located within the sterile field in which a surgery is performed, while the personal surgical center, and the hospital/medical office systems can be located outside the sterile field.

Biological Tissue Cutting Device

With reference to FIGS. 6 and 14, in certain embodiments, the biological tissue cutting and/or aspiration handpiece (for example, vitrectomy handpiece or other like handpieces) is portable, lightweight and can be powered by battery to power the cutter and/or aspiration. It can be used in the field, offices, surgery centers and operating rooms. The biological tissue cutting and/or aspiration handpiece may be used as a standalone instrument or in conjunction with the independent surgical center discussed above. The handpiece may be disposable and can be connected to the aspiration/infusion cassette, which provides aspiration pressure to the cutter. FIG. 6 illustrates on example of an aspiration/infusion cassette 100 with the infusion line 114 and the biological tissue cutting and aspiration handpiece 110. The left side of the cassette functions to provide aspiration pressure to the biological tissue cutting and aspiration handpiece, while the right side provides infusion.

In certain embodiments, for example, the biological tissue cutting and/or aspiration handpiece is a disposable handpiece such as that described in co-pending U.S. Patent Publication No. 2008-0208233 A1 (U.S. patent application Ser. No. 11/963,749) titled Disposable Vitrectomy Handpiece, filed Dec. 21, 2007, the entire content of which is incorporated herein by reference. In addition, the biological tissue cutting and/or aspiration handpiece can incorporate battery power or other power supply, and a flow controller/pinch valve. The handpiece may wirelessly communicate (for example, Bluetooth or the like) with other surgical instruments, an internal or external monitor or speaker, or a control center in the aspiration/infusion cassette. Alternatively, the handpiece may wirelessly communicate with a personal surgical center and/or an independent surgical center. Surgical parameters (for example, cut speed, frequency, aspiration pressure/flow rate) may be controlled directly on the handpiece, or via a foot pedal wirelessly connected to the handpiece. Such parameters may control a cutting tip, aspiration pump, and the like. The drive circuitry may be incorporated directly in the handpiece, in the surgical tray, or aspiration/infusion cassette depending on how the handpiece is powered (for example, by battery or through the aspiration/infusion cassette).

As noted above, according to certain embodiments, the biological tissue cutting and/or aspiration handpiece can be a stand-alone instrument, not used with an external control center. In certain embodiments, the handpiece can be used in conjunction with other standalone instrumentation, such as an illumination device. The controls for the handpiece are located on the handpiece itself, eliminating the need for a surgical console. The handpiece itself or the surgical tray may have a display or speaker to inform the surgeon of current surgical settings and instrument faults. According to certain embodiments, the handpiece includes a control unit or processing unit which may be, for example, a microprocessor based unit, an ASIC, or the like, and other circuitry.

In certain embodiments, the biological tissue cutting and/or aspiration handpiece can be used in conjunction with an aspiration/infusion cassette that includes a control center or in conjunction with an external, laptop control center. Although it may be possible to plug the system into an outlet, battery power can enable better maneuverability of the handpiece. The battery may be placed inside the handpiece, surgical tray or at the aspiration/infusion cassette itself. When the battery is placed inside the handpiece, it adds weight and size to the unit, and can reduce maneuverability and ergonomics. The aspiration/infusion cassette can be larger and heavier because ergonomics on this instrument are not as critical. However, when the battery is placed at the aspiration/infusion cassette or surgical tray, an electrical line would need to be tethered to the handpiece along with the aspiration line.

The wireless control (for example, Bluetooth) may be mounted in the handpiece, the aspiration/infusion cassette, the surgical tray, or all of the above. If the handpiece uses battery power and includes no link to the aspiration cassette or surgical tray, wireless communication will generally be within the handpieces, surgical tray, and other devices. However, if there is a direct-wired link between the two, wireless communications may then be with certain devices, for example the surgical tray. In certain embodiments, the wireless communication will be within the aspiration/infusion cassette or surgical tray to reduce the weight of the handpiece. In certain embodiments, the battery/power source for the biological tissue cutting and/or aspiration handpiece, the network communication, and the aspiration originate from the surgical tray through a direct wire connection.

In certain embodiments, the handpiece may include a display and/or speaker for relaying information regarding instrument status, fault, cut speed, or the like. For example, the handpiece may include a LED and/or speaker on the handpiece itself. In certain embodiments, the instrument and operation information may also be shown on a display or speaker on the surgical tray or may be displayed on a personal surgical center or a laptop center to allow the surgeon to more easily review such information.

When used in conjunction with a personal surgical center or a laptop center, the biological tissue cutting and/or aspiration handpiece may communicate with the personal surgical center or the laptop directly or indirectly through the independent surgical tray or surgical tray. The personal surgical center or laptop center can indicate the instrument and operation information, such as current cut speed, battery life (if applicable), any faults, or any other indicator or status information. It may also receive additional information, such as the maximum cut speed permissible and other surgical parameters. Upon startup, the biological tissue cutting and/or aspiration handpiece can identify itself to the independent surgical center, and/or personal surgical center and/or laptop center, and indicate whether it has been used before. If flow sensing or flow control is used, the sensors and actuators may be placed close to or directly on the biological tissue cutting and/or aspiration handpiece.

Personal Surgical Center

Figure 14A:
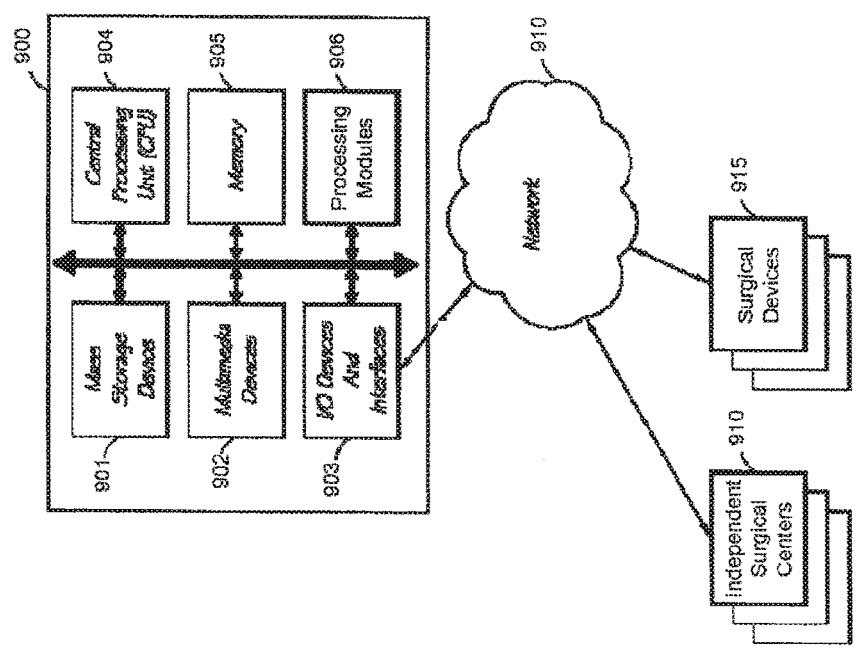
FIG. 14A is a block diagram depicting one embodiment of a computer hardware system configured to run software for implementing one or more embodiments of the system described herein, for example, the personal surgical center.

With reference to FIG. 14A, there is illustrated one embodiment of a computer system and/or device for the personal surgical center. FIG. 14A illustrates a block diagram of one embodiment of a computing system (which can be a fixed system or mobile device) that is in communication with one or more independent surgical centers 910 and/or one or more surgical devices 915 via one or more networks 910. The computing system 900 may be used to implement one or more of the systems and methods described herein. In addition, in one embodiment, the computing system 900 may be configured to process status data and/or information from surgical devices. While FIG. 14A illustrates one embodiment of a computing system 900, it is recognized that the functionality provided for in the components and modules of computing system 900 may be combined into fewer components and modules or further separated into additional components and modules.

In one embodiment, the system 900 comprises processing and analysis modules 906 that carry out the functions, methods, and/or processes described herein. The processing and analysis modules 906 may be executed on the computing system 900 by a central processing unit 904 discussed further below.

Computing System Components

In one embodiment, the processes, systems, and methods illustrated above may be embodied in part or in whole in software that is running on a computing device. The functionality provided for in the components and modules of the computing device may comprise one or more components and/or modules. For example, the computing device may comprise multiple central processing units (CPUs) and a mass storage device, such as may be implemented in an array of servers.

In one embodiment, the computing system 900 also comprises a laptop computer suitable for controlling and/or communicating with databases, performing processing, and generating reports from databases. The computing system 900 also comprises a central processing unit ("CPU") 904, which may comprise a microprocessor. The computing system 900 further comprises a memory 905, such as random access memory ("RAM") for temporary storage of information and/or a read only memory ("ROM") for permanent storage of information, and a mass storage device 901, such as a hard drive, diskette, or optical media storage device. Typically, the modules of the computing system 900 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The exemplary computing system 900 comprises one or more commonly available input/output (I/O) devices and interfaces 903, such as a keyboard, mouse, touchpad, and printer. In one embodiment, the I/O devices and interfaces 903 comprise one or more display devices or touch screen display devices, such as a monitor, that allows the visual presentation of data to a user. More particularly, a display device provides for the presentation of GUIs, application software data, and multimedia presentations, for example. In the embodiment of FIG. 14A, the I/O devices and interfaces 903 also provide a communications interface to various external devices. The computing system 900 may also comprise one or more multimedia devices 902, such as speakers, video cards, graphics accelerators, and microphones, for example.

Computing System Device/Operating System

The computing system 900 may run on a variety of computing devices, such as, for example, a server, a Windows server, a Structure Query Language server, a Unix server, a personal computer, a mainframe computer, a laptop computer, a cell phone, a personal digital assistant, a kiosk, an audio player, and so forth. The computing system 900 is generally controlled and coordinated by operating system software, such as z/OS, Windows 95, Windows 98, Windows NT, Windows 2000, Windows XP, Windows Vista, Linux, BSD, SunOS, Solaris, or other compatible operating systems. In Macintosh systems, the operating system may be any available operating system, such as MAC OS X. In other embodiments, the computing system 900 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 14A, the computing system 900 is coupled to a network 910, such as a LAN, WAN, or the Internet, for example, via a wired, wireless, or combination of wired and wireless, communication link 915. The network 910 communicates with various computing devices and/or other electronic devices via wired or wireless communication links. In the exemplary embodiment of FIG. 14A, the network 910 is communicating with one or more independent surgical centers 910 and/or one or more surgical devices 915.

Computing system may comprise a browser module or other output module that may be implemented as a combination of an all points addressable display such as a cathode-ray tube (CRT), a liquid crystal display (LCD), a plasma display, or other types and/or combinations of displays. In addition, the browser module or other output module may be implemented to communicate with input devices 903 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module or other output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 900 may comprise a physical or logical connection established between a remote microprocessor and a mainframe host computer for the express purpose of uploading, downloading, or viewing interactive data and databases on-line in real time or periodic basis. The remote microprocessor may be operated by an entity operating the computer system 900, including the client server systems or the main server system, an/or may be operated by one or more of the surgical devices 915 and/or one or more of the independent surgical centers 910.

Other Systems

In addition to the systems that are illustrated in FIG. 14A, the network 910 may communicate with other data sources or other computing devices, for example billing systems or hospital information systems. The computing system 900 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

In some embodiments, the acts, methods, and processes described herein are implemented within, or using, software modules (programs) that are executed by one or more general purpose computers. The software modules may be stored on or within any suitable computer-readable medium. It should be understood that the various steps may alternatively be implemented in-whole or in-part within specially designed hardware. The skilled artisan will recognize that not all calculations, analyses and/or optimization require the use of computers, though any of the above-described methods, calculations or analyses can be facilitated through the use of computers.

Example Process Flow

Figure 15:
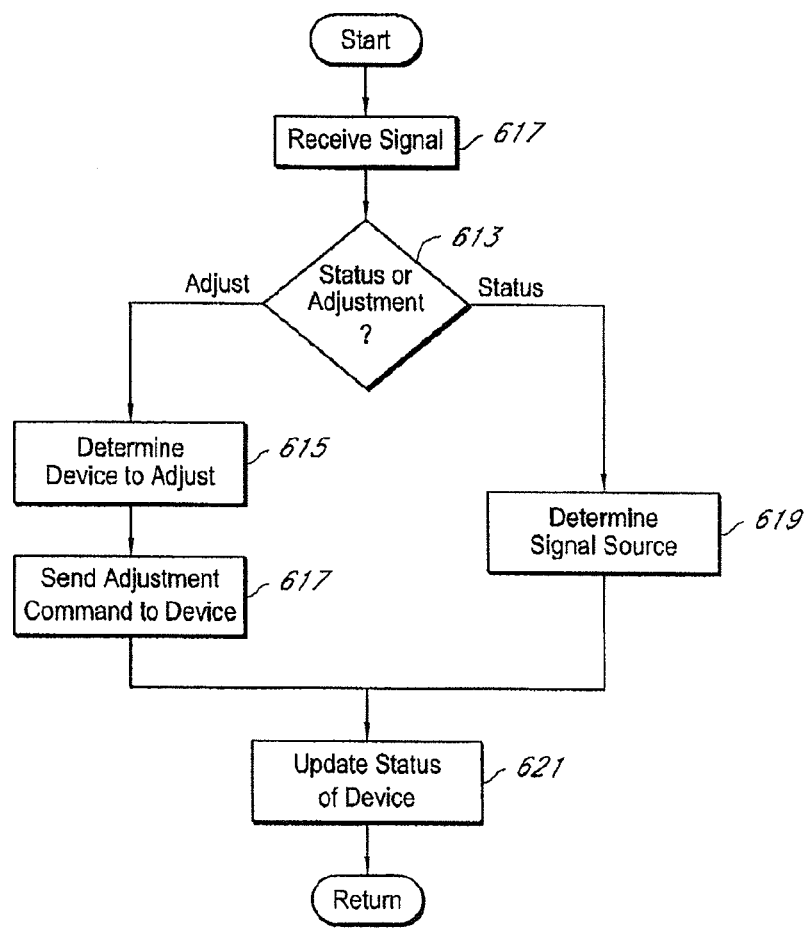
FIG. 15 is a flow diagram of various processes executed by the processing unit and/or the surgical tray in accordance with a preferred embodiment of the invention.

FIG. 15 is a flow diagram of a process executed by the processing unit 1446 of an independent surgical center in accordance with an embodiment of the invention.

In some embodiments, the process of FIG. 15 represents the process which is performed by the processing unit housed or received in the sterile surgical tray as described herein. In some embodiments of the invention, the process may be performed in another instrument or component of the system, based on where the processing unit is located in the system. In some embodiments, the system may include multiple processing units, and the process of FIG. 15 may be performed by one or more of the multiple processing units.

In block 611, the process receives a signal from an instrument in communication with the independent surgical center. In the embodiment, the tray may receive the signals from an instrument through a wired connection, for example, the handpiece, or may receive the signals from an instrument through a wireless connection, for example, from the illumination device.

In block 613, the process determines whether the received signal is a status update signal or an adjustment request signal. In some embodiments, the processing unit may be used to adjust operation parameters of selected instruments, and may also be used to process and communicate to a user the status of the same or other instruments. If the processing unit determines that the signal is an adjustment request signal, the process proceeds to block 615. If the processing unit determines that the signal is a status update signal, the process instead proceeds to block 619.

In block 615, the process determines the device for which the adjustment signal is directed. In some embodiments, the adjustment signal may be received by a user control directly connected to the processing unit. For example, the adjustment signal may originate from a user control controlling the infusion device located alongside the processing unit in the tray. In other embodiments, the adjustment signal may be received wirelessly from a user control located on a remote instrument, for example, a foot pedal associated with the tray. Some of the adjustment requests may be meant for the device or component from which the signal originated, while some other of the adjustment requests may be meant for a different device, whether it is a device on the tray or on a completely separate instrument in the surgical system. Regardless of the source of the adjustment signal, the processing unit determines the intended destination device or instrument.

In block 617, the process sends an adjustment command to the destination device or instrument. Depending on the configuration of the system, the adjustment command may be an unaltered adjustment signal, where the processing unit acts as a switch or routing device for the system, or the adjustment command may be a wholly new command signal generated by the processing unit based on a received adjustment request signal, for example, a received signal as was described above with respect to block 611. In most embodiments of the system, after an adjustment command is sent to a respective device or instrument, the operational settings or parameters of the device are adjusted in accordance with the adjustment command.

If the signal is a status update signal, the process, in block 619, determines the source of the status update signal. In most embodiments, status update signals include status update information of the device from which the status update signal originated. The status update information may include various information about an originating device, for example, current settings, operating parameters, remaining power levels, instrument fault conditions, and other information. Status information for each specific instrument in the system is different depending on the functionality of the instrument. For example, a handpiece may provide status of cut speed of a cutter or aspiration levels, whereas an illumination device may provide illumination level status.

In block 621, the process updates the status of a device or instrument. Whether the originally received signal was an adjustment signal or a status update signal, the processing unit of the system may update status information pertaining to the received signal. In cases where the signal was an adjustment signal, the processing unit may update the status information of the destination device to which the adjustment request was sent. In cases where the signal was a status update signal, the processor may directly update the status information of the device from which the status update signal originated, based on the contents of the status update signal. The processing unit may display the status updates on, for example, a monitor located on the instrument housing the processing unit. Alternatively, the status updates may be expressed visually through changes to, for example, LED indicators, or aurally through, for example, audio alerts outputted through available speakers. In some embodiments, visual or aural status indicators may be available on various other instruments of the system in addition to, or in lieu of, the instrument housing the processing unit. In these embodiments, the processing unit may send the status update information to an appropriate instrument for output or user feedback purposes. According to one embodiment of the invention, the update information is transmitted to the personal surgical center for logging in a log file generated for the surgical procedure. After the status updates have been applied to or recorded by the system, the process returns.

Safety Mechanism Procedures

Figure 16:
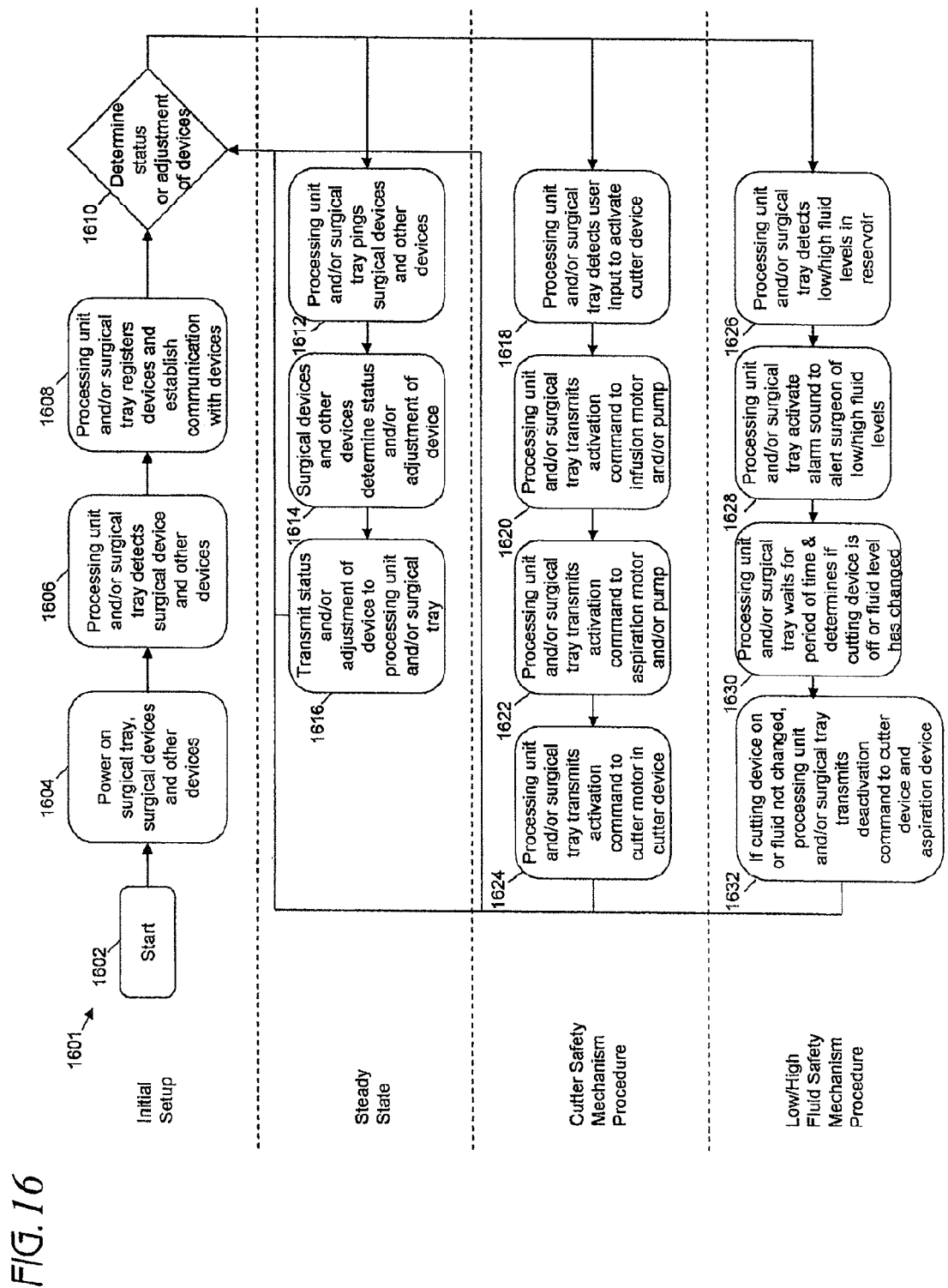
FIG. 16 is a flow diagram of a process executed by the processing unit of the independent surgical center in accordance with a preferred embodiment of the invention.

As illustrated in FIG. 16, in certain embodiments, the independent surgical center 1402 and/or the processing unit 1446 and/or the personal surgical center 1410 as described herein can be configured to receive status and/or adjustment data from, or determine the status of the various surgical and/or devices 1401. In analyzing and/or monitoring the status of the various surgical and/or devices 1401, the independent surgical center 1402, and/or the processing unit 1446, and/or personal surgical center 1410 can be configured to invoke various safety mechanism procedures, for example but not limited a cutter safety mechanism procedure and a low fluid safety mechanism procedure.

With reference to FIG. 16, the illustrated process 1601 can be segmented into at least four different stages, initial setup, steady state, cutter safety mechanism procedure, and the low fluid safety mechanism procedure. Process 1601 starts at block 1602. The user and/or surgeon powers on the independent surgical center, the surgical and/other devices at block 1604. In powering on the independent surgical center, at block 1606 the processing unit and/or the electronics in the independent surgical center searches, detects, and/or locates available surgical and/or other devices to be employed during the surgery. At block 1608, the processing unit and/or the independent surgical center registers the available surgical and/or other devices for the surgery. In registering, the surgical and/or devices can communicate and/or send to the processing unit and/or the independent surgical center parameter and/or identification information, including but not limited to surgical device identification number, lot number, part number, surgical device name and/or type, current status of device, available options on device (for example, on or off; low, medium, or high speed; or the like). After registering and/or establishing communication with all the surgical and/or other devices, the processing unit and/or the independent surgical center obtains and/or receives periodic information/data from the surgical and/other devices in order to determine at block 1610 the status or adjustments made in or to the surgical and/or other devices.

In reference to FIG. 16, in one embodiment, processing unit and/or the independent surgical center enters a steady state, wherein the processing unit and/or independent surgical center pings, requests, or receives data and/or information from the surgical and/or other devices at block 1612. At block 1614, the surgical and/or other devices can be configured to gather, obtain, and/or analyze status and/or other data for sending or transmitting to the processing unit and/or independent surgical center. The surgical and/or other devices can be configured to send or transmit, on a real-time, substantially real-time, periodic basis, data and/or other information to the independent surgical center at block 1616, wherein the data and/or other information can comprise without limitation device status information (for example, on or off, activated or deactivated, speed levels, temperature, battery levels, elapsed time, fluid levels, warning and/or error messages, or the like), user inputted adjustment data, device data, or the like. After sending or transmitting the data, the procedure returns to block 1610 to repeat the process.

With reference to FIG. 16, in certain embodiments, the processing unit and/or independent surgical tray can detect when the user or surgeon has activated the cutter device by receiving a status message from the cutter device at block 1618. In certain embodiments, the processing unit and/or the independent surgical center can initiate a cutter safety mechanism procedure before and/or while allowing the cutter device to be activated. In certain embodiments, before allowing the cutter device to be activated, or simultaneously with the activation of the cutter, the processing unit and/or the independent surgical center at block 1620 can be configured to transmit an activation command or signal to the infusion motor and/or pump to initiate delivery of infusion fluids to the surgical site. In certain embodiments, before allowing the cutter device to be activated, or simultaneously with the activation of the cutter, the processing unit and/or the independent surgical center at block 1622 can also be configured to transmit an activation command or signal to the aspiration motor and/or pump to generate a vacuum for removing excess fluid and/or tissue/debris from surgical site, and/or to prime the fluid in the cutter before cutting begins. In certain embodiments, the processing unit and/or the independent surgical center at block 1624 can be configured to transmit an activation command or signal to the cutter motor device. After sending or transmitting the activation commands or signals, the procedure returns to block 1610 to repeat the process.

The cutter safety mechanism procedure can prevent surgical errors and/or harm to the patient by ensuring that the necessary surgical and/or devices are activated before cutting is initiated. For example, in various eye surgeries, the infusion motor must be activated prior to cutting to prevent the collapse of the eye caused by reduced internal eye pressure due to aspirated or leaked vitreous. The foregoing procedure can reduce the complexity of the surgery for the surgeon by reducing the number of steps to activate the various necessary devices for the surgery.

In reference to FIG. 16, in certain embodiments, the processing unit and/or independent surgical tray at block 1626 can detect when fluid levels are low and/or high in the various fluid reservoirs by receiving a status message from a fluid chamber device, for example, infusion reservoir 104. In certain embodiments, the processing unit and/or the independent surgical center can initiate a low/high fluid safety mechanism procedure before and/or while the cutter device is activated. In certain embodiments, before allowing the cutter device to be activated, or while the cutter device is activated, the processing unit and/or the independent surgical center at block 1628 can initiate and/or activate an alarm sound circuitry within the independent surgical center and/or other surgical device, wherein an audible sound/alarm would be generated to alert the user/surgeon of the low and/or high fluid levels in the various reservoir chambers. The processing unit and/or the independent surgical center at block 1630 can also be configured to wait for a period of time (predetermined or user defined), for example, ten seconds, ten minutes, or the like, before receiving and/or obtaining status information from the cutting device. In other embodiments, the processing unit and/or the independent surgical center can also obtain data and/or information from other surgical devices, such as the fluid reservoir chambers to determine if the fluid levels have been changed. If the cutting device is on and/or the fluid levels have not changed and/or have become worse, then the processing unit and/or the independent surgical center at block 1632 can transmit and/or send a deactivation command to the cutter device and/or the aspiration device. In certain embodiments, the processing unit and/or the independent surgical center will continue to maintain infusion to prevent collapse of the eye. After sending or transmitting the deactivation commands or signals, the procedure returns to block 1610 to repeat the process.

The high/low safety mechanism procedure can prevent surgical errors and/or harm to the patient by ensuring that the necessary reservoir chambers have sufficient fluid levels during the surgery. For example, in various eye surgeries, the infusion of the eye should be continuous to prevent collapse of the eye due to leakage/remove of vitreous fluids, and therefore, low levels of infusion fluids in the infusion reservoir can pose a risk for eye collapse during surgery. The foregoing procedure can also reduce the complexity of the surgery for the surgeon by reducing the need for the surgeon and/or the assistant to constantly monitor the fluid levels of the reservoir chambers.

As with the other embodiments disclosed above, FIGS. 17-21 disclose a surgical tray system 1700 configured to allow a surgeon or other user to directly monitor and/or directly control tools and other instruments associated with the surgical tray system 1700 while not having to move away from and/or to look substantially away from the surgical field. A surgeon or other user using the surgical tray systems described herein would not need to or would not substantially need to rely on and/or provide verbal instructions to an assistant or scrub in order to make various system adjustments.

Figure 17:
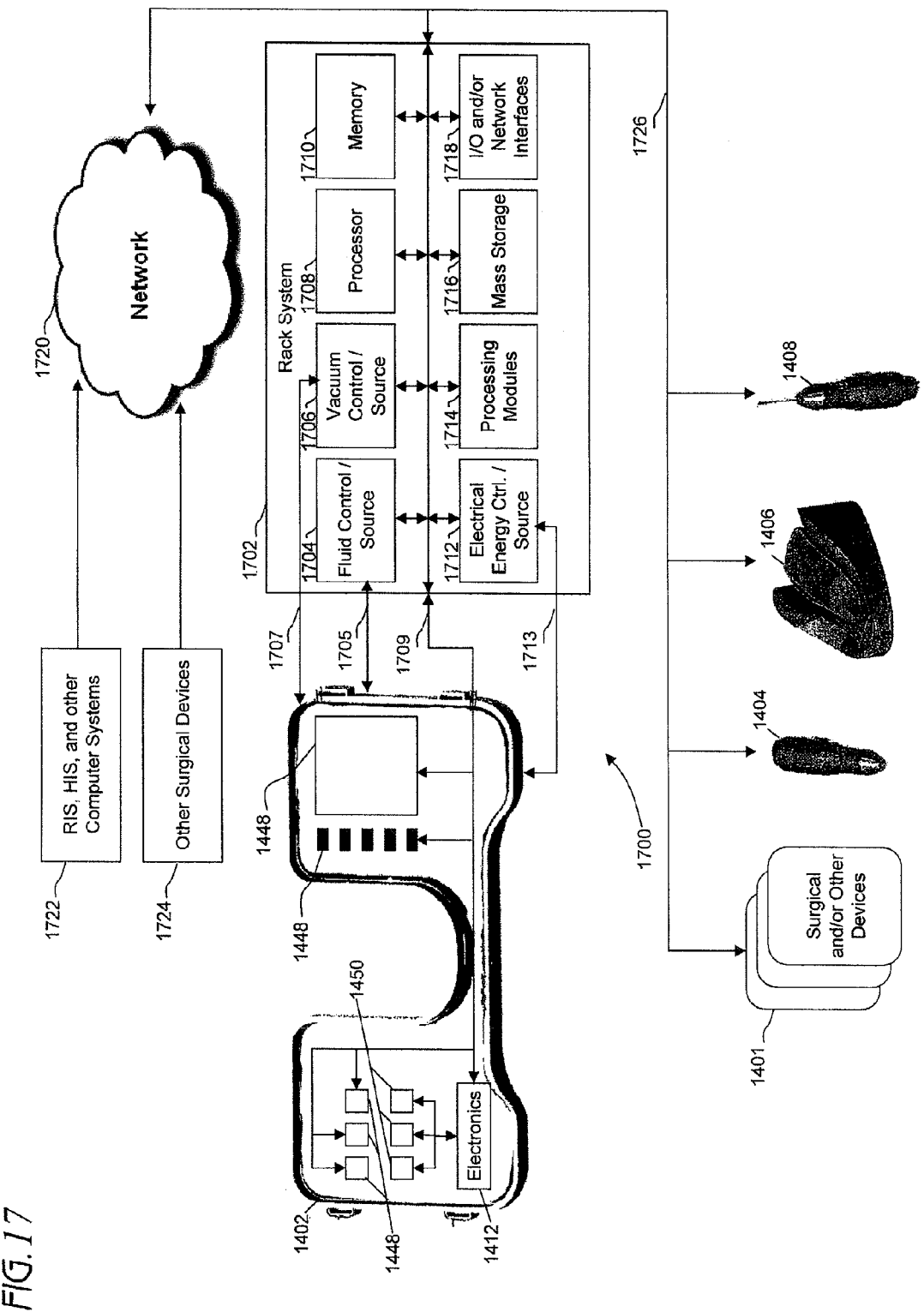
FIG. 17 is a schematic view of an embodiment of the sterile surgical tray in communication with a rack system.

As illustrated in FIG. 17, the surgical tray system 1700 can comprise at least one display to allow the surgeon or other users to directly monitor the tools and other instruments associated with the surgical tray system 1700. With the at least one display within the surgical field and/or substantially within, near, adjacent, and/or proximal to the same visual plane, area, and/or field as the surgical site, the surgeon and/or user would not need to substantially look away from the surgical site. For example, in certain embodiments, the surgeon and/or other user would genearlly only need to look to the side of the surgical site, and would generally not need to look substantially up and/or away from the surgical site to view a monitor or other display. In certain embodiments, the surgical tray system 1700 comprises at least one controller (for example, button, knob, switch, user input interface, or the like) to receive user input and to allow the surgeon or other user to directly control surgical tools, or other instruments, including but not limited to a fluid source, a vacuum source, a light source, a electrical energy source, or the like. With the at least one controller within the surgical field and/or substantially within, near, adjacent, and/or proximal to the same visual plane, area, and/or field as the surgical site, the surgeon and/or user would neither need to substantially look away from the surgical site, nor rely on and/or provide verbal instructions to an assistant in order to make various adjustments to the system, tools, and/or other instruments. In certain embodiments, the at least one controller is positioned on, within, combined with, embedded in, coupled to a surgical device, for example but not limited to, the cutting device 1408 or other handheld devices. In certain embodiments, user input can be received at or from or on or through a controller on a surgical device or on a surgical tray. User input received at, or by, a controller on the surgical device can be transmitted (through a wired or wireless connection) directly to a rack system or to the rack system through the surgical tray.

With further reference to FIG. 17, in certain embodiments, the sterile surgical tray 1042 comprises at least one controller 1450. The at least one controller 1450 can be connected to, be in electrical communication with, and/or be coupled to a rack system 1702 via communications link 1709 (wired and/or wireless). Examples of wireless communication links include but are not limited to radio frequency (RF), infrared or other optical links, or the like. The at least one controller 1450 can include but is not limited to a switch, knob, button, or other mechanism for capturing user input. In certain embodiments, the sterile surgical tray 1042 comprises at least one display 1448. The at least one display 1448 can be connected to, be in electrical communication with, and/or be coupled to a rack system 1702. The at least one display 1448 can include but is not limited to a liquid crystal display (LCD), a light emitting diode (LED), a light, a meter, an indicator, or other mechanism for outputting data, information, status, and/or indication to the user.

The rack system 1702 can comprise, for example, but is not limited to, a general purpose computer, a specialized purpose computer, or other computer system connected to, in communication with, or coupled to other systems, apparatuses, devices, and/or hardware, including but not limited to a fluid control apparatus and/or fluid source 1704, a vacuum control apparatus and/or vacuum source 1706, a processor 1708, memory 1710, electrical energy control apparatus and/or source 1712, processing modules 1714, mass storage 1716, and/or input/output (I/O) interfaces and/or network interfaces 1718.

The rack system 1702 can also comprise a fluid control apparatus and/or a fluid source 1704. The rack system 1702 can be connected to an external fluid source wherein the fluid control apparatus 1704 is configured to control the flow of fluid into the sterile surgical tray 1042 through tube 1705. Alternatively, the rack system 1702 can comprise a fluid source 1704 wherein the rack system is configured to control the flow of fluid into the sterile surgical tray 1042 through tube 1705. In certain embodiments, the surgeon and/or other user can control the fluid control apparatus and/or the fluid source 1704 by adjusting the at least one controller on the sterile surgical tray 1042 and/or by adjusting a controller on a surgical instrument, handheld device, handpiece, or the like that is near, adjacent, around, or proximal to the sterile surgical tray. The rack system 1702 can comprise vacuum control apparatus and/or a vacuum source 1706. The rack system 1702 can be connected to an external vacuum source wherein the vacuum control apparatus 1706 is configured to control the amount or strength of vacuum applied or delivered to the sterile surgical tray 1042 through tube 1707. Alternatively, the rack system 1702 can comprise a vacuum source 1706 wherein the rack system is configured to control the amount or strength of vacuum into the sterile surgical tray 1042 through tube 1707. In certain embodiments, the surgeon and/or other user can control the vacuum control apparatus and/or the vacuum source 1706 by adjusting the at least one controller on the sterile surgical tray 1042.

The rack system 1702 can comprise a processor 1708. The processor 1708 can be configured to process user input received from the user through the at least one controller 1450. The processor 1708 can be configured to process output data for displaying to the user through the at least one display. The processor 1708 can be configured to control and/or send instructions to tools, instruments, modules, components, and/or devices associated with the rack system 1702 and/or the surgical tray system 1700. The rack system 1702 can comprise memory for storing data and/or instructions to be processed by the processor 1708. The rack system 1702 can comprise an electrical energy control apparatus and/or an electrical energy source 1712. The rack system 1702 can be connected to an external electrical energy source wherein the electrical energy control apparatus 1712 is configured to control the flow of electrical energy to and/or allow electrical energy to be directed into the sterile surgical tray 1042 through wires 1713. Alternatively, the rack system 1702 can comprise an electrical energy source 1712 wherein the rack system is configured to control the flow of electrical energy into the sterile surgical tray 1042 through wires 1713. In certain embodiments, the surgeon and/or other user can control the electrical energy control apparatus and/or the fluid source 1712 by adjusting the at least one controller 1450 on the sterile surgical tray 1042.

The rack system 1702 can comprise processing modules 1714. Processing modules 1714 can include but is not limited to a processing apparatus for controlling a light source, an electric motor, a pressure detection apparatus, and any other apparatus. The rack system 1702 can comprise a mass storage apparatus 1716 for storing software instructions, and/or data processed by the processor 1708, and/or data received from the user and/or the tools and instruments associated with the surgical tray system 1700. The rack system 1702 can comprise an input/output (I/O) and network interface apparatus for communicating, via a wired and/or wireless connection, with other computer systems through a network 1720, and/or with other instruments 1401 associated with the surgical tray system 1700 through the communications link 1726.

For example, a surgeon and/or other user can control a cutting device 1408 by providing input or instructions through the at least one controller 1450 on the sterile surgical tray 1042, wherein the at least one controller 1450 transmits a signal to the rack system 1702 through the communications link 1709 (wired or wireless). Alternatively, a surgeon and/or other user can control a cutting device 1408 or other device by providing input or instructions through the at least one controller 1450 on the cutting device 1408 or other device, wherein the at least one controller 1450 transmits a signal to the rack system 1702 through the communications link 1709 (wired or wireless), wherein the signal can be transmitted directly to the rack system 1702 or to the rack system 1702 through the sterile surgical tray 1042. The rack system 1702 can be configured to process the user input and to send a signal to the cutter device 1408 through communications link 1726 (wired or wireless). The cutter device 1408 can be configured to return status data to the rack system 1702 via the communications link 1726, wherein the rack system 1702 is configured to process the status data. The rack system 1702 can be configured to display the processed status data to the surgeon and/or other user through the at least one display 1448. In this configuration, the sterile surgical tray 1042 is configured to allow the surgeon and/or other user to control and/or adjust from within the sterile surgical field various instruments and components associated with the surgical tray system 1700, while the processing of the instructions from the surgeon and/or the actual control of the various instruments and components is conducted or performed by the rack system 1702. In this configuration, the surgeon and/or other user can review and/or monitor on the sterile surgical tray 1042 the status of various instruments and components associated with the surgical tray system 1700, while the processing of the status data of the various instruments and components is conducted by the rack system 1702.

In certain embodiments, the sterile surgical tray 1042 is an extension of the rack system 1702. In certain embodiments, the sterile surgical tray 1042 is a "slave" of the rack system 1702, as opposed to a smart and/or independently operating surgical tray, as disclosed in other embodiments described herein. The sterile surgical tray 1042 can be configured to allow the surgeon to control and/or adjust the rack system 1702. The sterile surgical tray 1042 can be configured to display data processed and/or generated by the rack system 1702. In certain embodiments, the sterile surgical tray 1042 comprises electronics 1412, including but not limited to circuits, processors, memory, and other components for processing data received from the rack system via communications link 1709 (wired or wireless). The electronics 1412 can be configured to receive and/or process signals and/or input from the at least one controller 1450. The electronics 1412 can be configured to transmit, send, and/or communicate the signals and/or input to the rack system 1702 for further processing.

In certain embodiments, the rack system 1702 can be configured to communicate with radiology information system (RIS), hospital information system (HIS), and/or other computer systems 1722 through a network 1720. The rack system 1702 can be configured to store on or communicate to the RIS, HIS, and/or other computer systems 1722 data received from the sterile surgical tray 1402. Such data can include but is not limited to a serial number associated with the tray, a tray activation code or signal, a billing code or signal, or the like. In receiving any of the foregoing data, codes and/or signals, the RIS, HIS, and/or other computer systems 1722 can be configured to process a billing invoice or other signal or code. The rack system 1702 can be configured to store on or communicate to the RIS, HIS, and/or other computer systems 1722 data received from the user through the at least one controller 1450 on the sterile surgical tray 1402. The rack system 1702 can be configured to store on or communicate to the RIS, HIS, and/or other computer systems 1722 data displayed on the at least one display 1448. The rack system 1702 can be configured to store on the RIS, HIS, and/or other computer systems 1722 data received from the surgical tools and/or other devices 1401, 1404, 1406, 1408.

Figure 18:
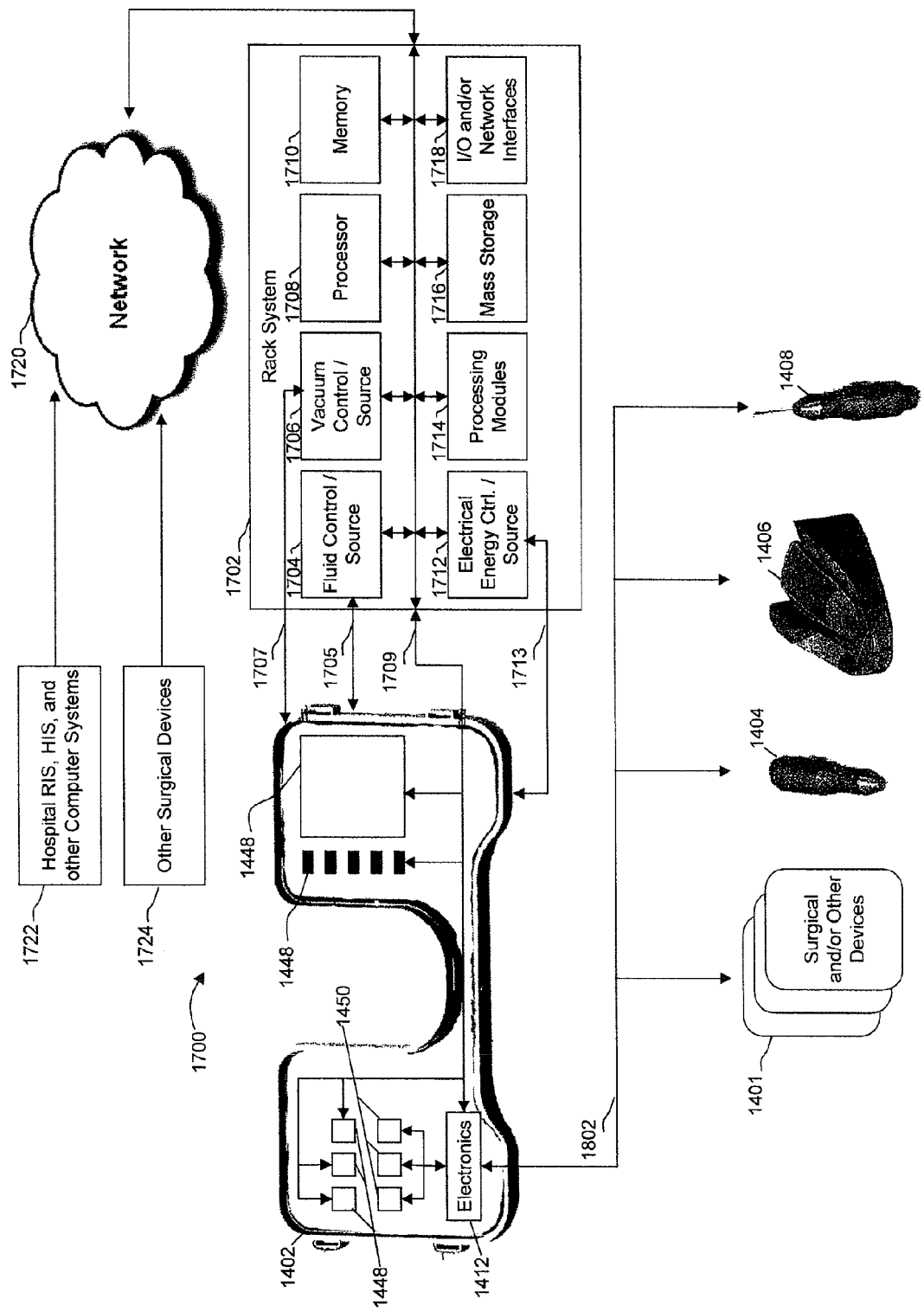
FIG. 18 is a schematic view of an alternative embodiment of the sterile surgical tray in communication with a rack system.

With reference to FIG. 18, there is illustrated another embodiment of the surgical tray system 1700 that is similar to the embodiment disclosed in FIG. 17. In the illustrated embodiment, the surgical tools and other devices 1401 (for example, the cutting device 1408) are connected to and/or are in direct communication with the sterile surgical tray 1402 through electronics 1412. The surgical tools and other devices 1401 can be configured to receive fluid, light, electrical energy, and/or vacuum through the sterile surgical tray 1402. Alternatively, the surgical tools and other devices 1401 can be configured to receive fluid, light, electrical energy, and/or vacuum from the rack system through connection tubes.

Figure 19:
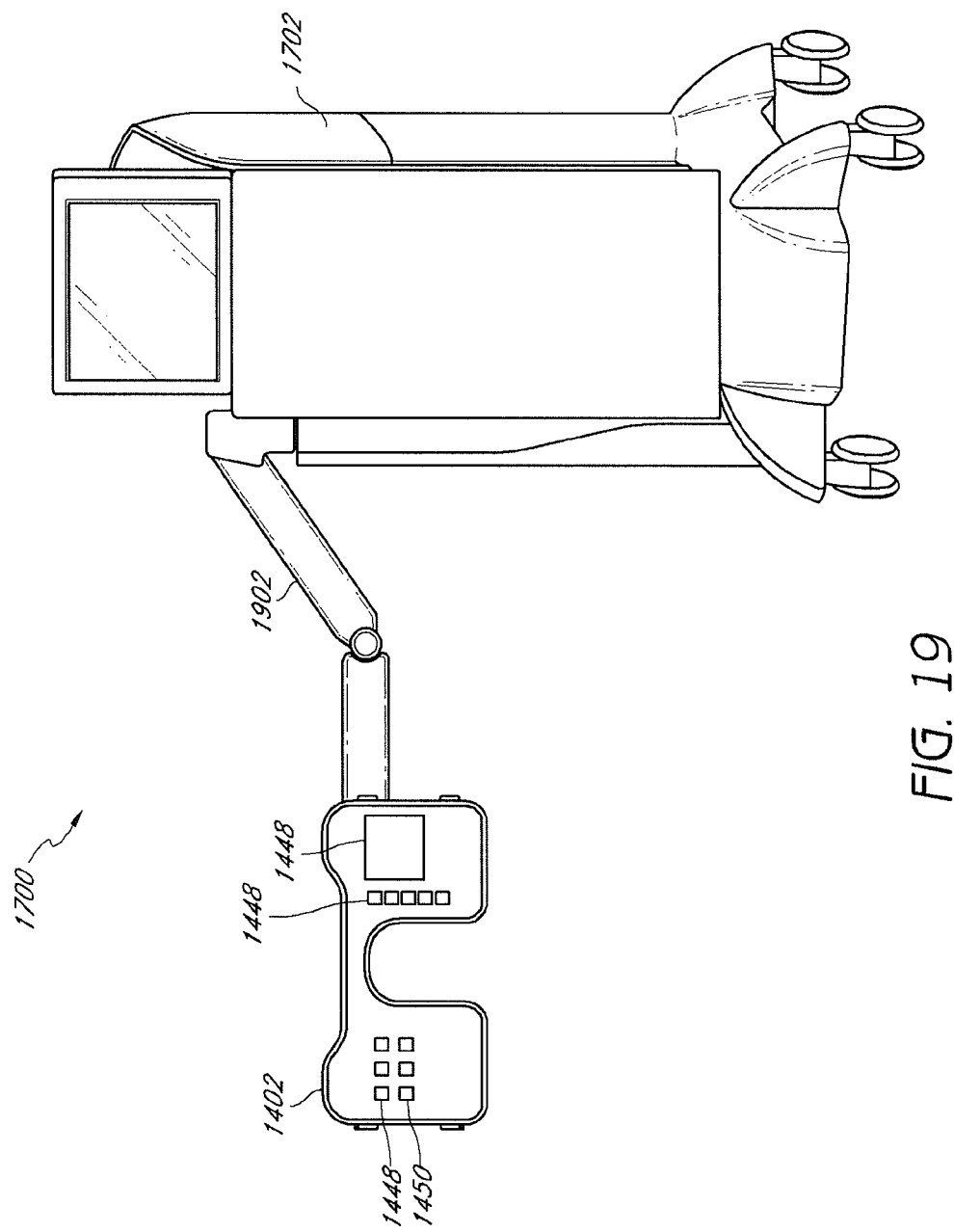
FIG. 19 is a schematic view of an embodiment of the sterile surgical tray connected to the rack system.
Figure 20:
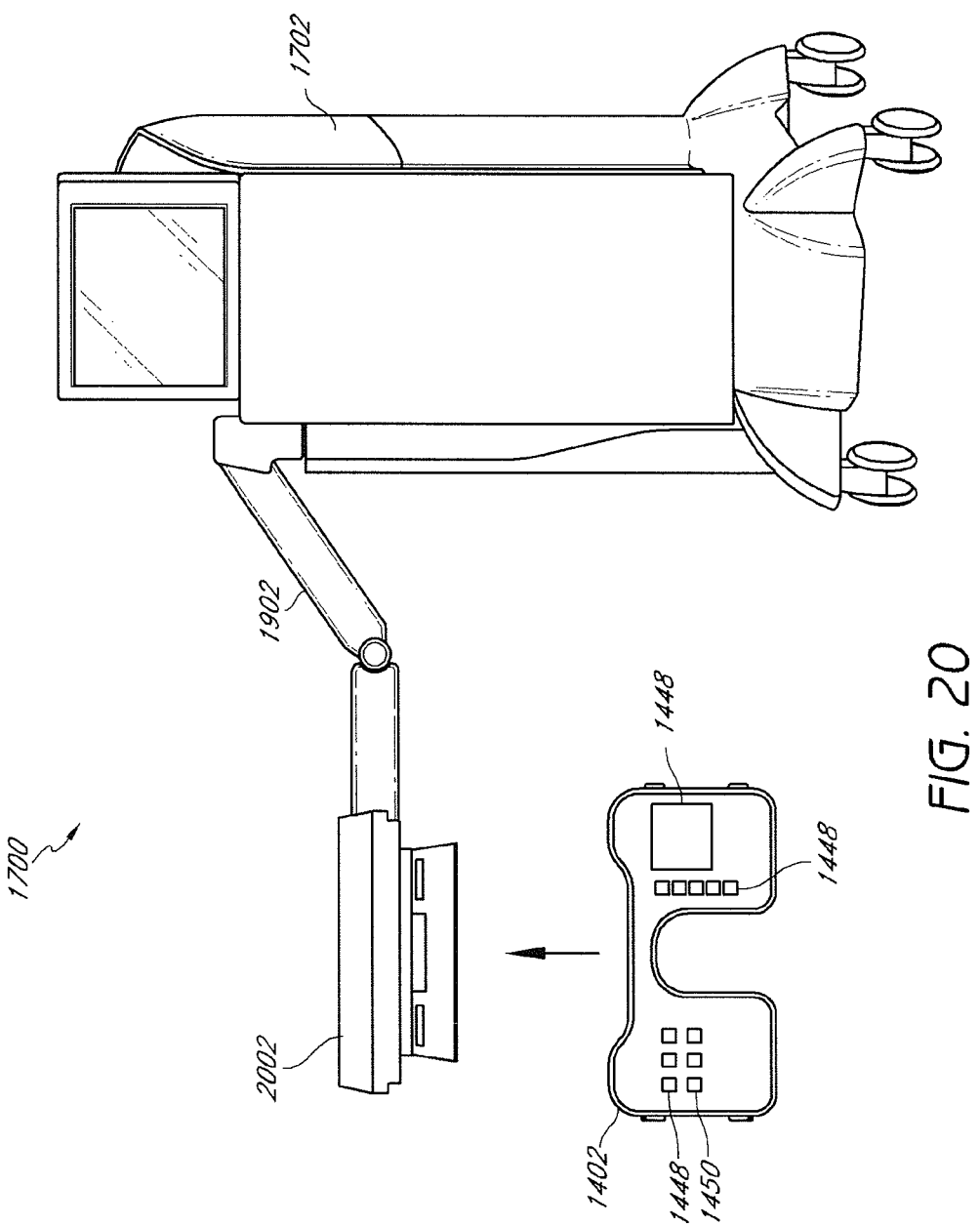
FIG. 20 is a schematic view of an embodiment of the sterile surgical tray connecting to the rack system through a docking station.
Figure 21:
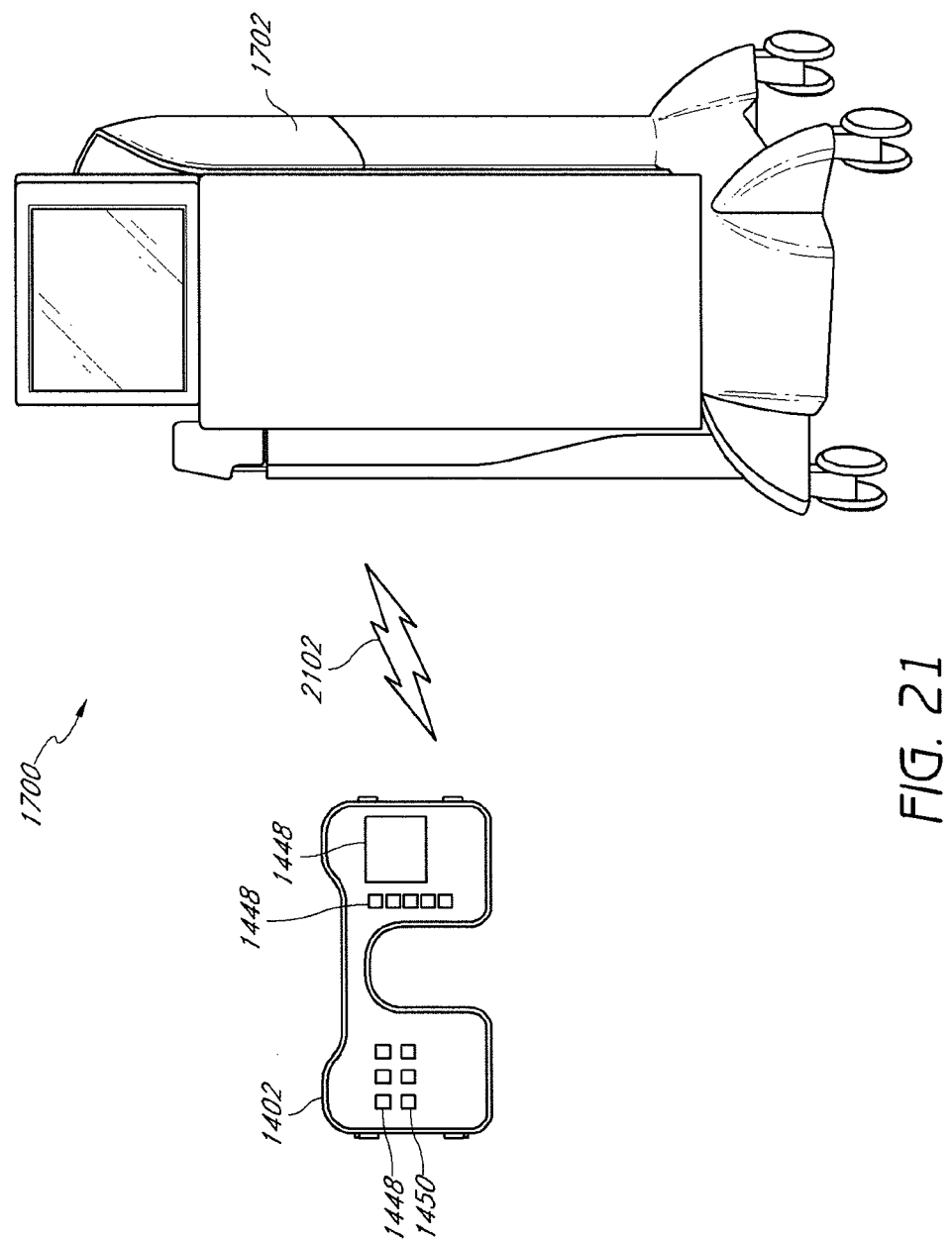
FIG. 21 is a schematic view of an embodiment of the sterile surgical tray communicating wirelessly with the rack system.

FIG. 19 illustrates another embodiment of the surgical tray system 1700 comprising a rack system 1702 connected and/or coupled to a sterile surgical tray 1402 via an arm 1902. The arm 1902 can include without limitation communication link 1709 and/or tubes 1705, 1707, and/or wires 1713, and any other connectors and/or conduits. As illustrated in FIG. 20, the surgical tray system 1700 can comprise a docking station 2002 connected or coupled to the arm 1902, which is connected or coupled to the rack system 1702. In certain embodiments, the sterile surgical tray 1402 comprises a connector or other apparatus for allowing the sterile surgical tray 1402 to dock with the docking station 2002. The docking station 2002 and/or the sterile surgical tray 1402 can comprise a locking mechanism for locking the sterile surgical tray 1402 to the docking station 2002. The docking station 2002 can comprise wire connectors to enable delivery of electrical energy or to enable electronic communication between the sterile surgical tray 1402 and the rack system 1702. The docking station 2002 can comprise tube connectors for allowing fluid and/or vacuum to be delivered to the sterile surgical tray 1402 from the rack system 1702. The docking station 2002 can comprise fiber optic connectors for allowing light to be delivered to the sterile surgical tray 1402 from the rack system 1702. With reference to FIG. 21, the sterile surgical tray 1402 can communicate wirelessly with the rack system 1702 through a wireless link 2102. In certain embodiments, the sterile surgical tray 1402 can be configured to receive data from the rack system 1702 through the wireless link 2102, wherein the at least one display 1448 is configured to display the data. In certain embodiments, the sterile surgical tray 1402 can be configured to receive input data from the surgeon or other user through the at least one controller 1450, wherein the sterile surgical tray 1402 can communicate or transmit the input data to the rack system 1702 through the wireless link 2102. The rack system 1702 can be configured to process the input data into instructions for controlling various surgical tools and/or other instruments associated with the surgical tray system 1700. The foregoing embodiments relating to the rack system 1702 can also be configured to communicate and/or combine and/or function with the smart surgical trays 10 disclosed herein.

In general, the term "module," as used herein, refers to logic embodied in hardware or firmware, or to a collection of software instructions, possibly having entry and exit points, written in a programming language, such as, for example, Java, C or C++, or the like. A software module may be compiled and linked into an executable program, installed in a dynamic link library, or may be written in an interpreted programming language such as, for example, BASIC, Perl, Lua, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

In some embodiments, the acts, methods, and processes described herein are implemented within, or using, software modules (programs) that are executed by one or more general purpose computers or other computer systems. The software modules may be stored on or within any suitable computer-readable medium. It should be understood that the various steps may alternatively be implemented in-whole or in-part within specially designed hardware. The skilled artisan will recognize that not all calculations, analyses and/or optimization require the use of computers, though any of the above-described methods, calculations or analyses can be facilitated through the use of computers.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although the inventions have been disclosed in the context of a certain preferred embodiments and examples and in the context of use with an endoilluminator, for example, an endoilluminator having an LED illumination light source, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above.

What is claimed is:

1. A sterile surgical tray system comprising:
  a sterile surgical tray for positioning in a surgical field, the sterile surgical tray including a plurality of surgical instruments sterilized with the sterile surgical tray;
  a rack system positioned apart from the sterile surgical tray outside the surgical field, the rack system configured to be in communication with the sterile surgical tray;
  at least one controller in the sterile surgical tray and configured to be an input mechanism in communication with at least one of the rack system and the plurality of surgical instruments;
  an arm mechanism coupled to the rack system;
  a docking station coupled to the arm mechanism and configured to receive the sterile surgical tray at a connector to enable communication between the rack system and the sterile surgical tray,
  wherein the rack system comprises a processor configured to process user input received at the sterile surgical tray through the at least one controller.

2. The sterile surgical tray system of claim 1, wherein the sterile surgical tray comprises a second processor configured to process user input received at the sterile surgical tray through the at least one controller.

3. The sterile surgical tray system of claim 1, wherein the at least one controller is disposed on a handpiece communicatively coupled to the sterile surgical tray.

4. The sterile surgical tray system of claim 3, wherein the handpiece is in communication with the rack system through the sterile surgical tray.

5. The sterile surgical tray system of claim 1, wherein the rack system further comprises a pump configured to pump fluid into the sterile surgical tray, and wherein the at least one controller is configured to control the pump.

6. The sterile surgical tray system of claim 5, wherein at least one of the plurality of surgical instruments is configured to receive the fluid.

7. The sterile surgical tray system of claim 1, wherein the rack system further comprises a light source configured to be controlled by the at least one controller of the sterile surgical tray.

8. The sterile surgical tray system of claim 7, wherein the light source is configured to direct light into the sterile surgical tray.

9. The sterile surgical tray system of claim 8, wherein at least one of the plurality of surgical instruments is configured to receive the light.

10. The sterile surgical tray system of claim 7, wherein the light source is configured to direct light into at least one of the plurality of surgical instruments.

11. The sterile surgical tray system of claim 1, wherein the rack system further comprises a pressurized gas source configured to be controlled by the at least one controller of the sterile surgical tray.

12. The sterile surgical tray system of claim 11, wherein the pressurized gas source is configured to direct pressurized gas into the sterile surgical tray.

13. The sterile surgical tray system of claim 12, wherein at least one of the plurality of surgical instruments is configured to receive the pressurized gas to drive a pneumatic drive in the surgical instrument.

14. The sterile surgical tray system of claim 11, wherein the pressurized gas source is configured to direct pressurized gas into at least one of the plurality of surgical instruments to drive a pneumatic drive in the at least one surgical instrument.

15. The sterile surgical tray system of claim 1, wherein the rack system further comprises an electrical energy source configured to be controlled by the at least one controller in the sterile surgical tray.

16. The sterile surgical tray system of claim 15, wherein the electrical energy source is configured to direct electrical energy to the sterile surgical tray.

17. The sterile surgical tray system of claim 16, wherein at least one of the plurality of surgical instruments is configured to receive the electrical energy.

18. The sterile surgical tray system of claim 15, wherein the electrical energy source is configured to direct electrical energy to at least one of the plurality of surgical instruments.

19. The sterile surgical tray system of claim 1, wherein the plurality of surgical instruments comprises a plurality of ophthalmic surgical instruments prepackaged and sterilized with the sterile surgical tray.

20. The sterile surgical tray system of claim 19, wherein at least one of the plurality of ophthalmic surgical instruments is a tissue isolation instrument, an aspiration instrument, or an infusion instrument.

21. The sterile surgical tray system of claim 20, wherein the tissue isolation instrument is at least one of a phacoemulsification device, a vitreous cutter, a fragmentation device, a lens cutting device, a scissors, and a cautery knife.

22. The sterile surgical tray system of claim 1, wherein the sterile surgical tray comprises a geometric shape for positioning around a head of a patient during an ophthalmic surgery.

23. The sterile surgical tray system of claim 1, wherein the docking station is configured to establish a connection between the sterile surgical tray and the rack system.

24. The sterile surgical tray system of claim 23, wherein the connection comprises at least one of an electrical connection, a fluid connection, and a vacuum connection.

25. The sterile surgical tray system of claim 1, further including at least one display in the sterile surgical tray and wherein the rack system is configured to be in communication with the at least one display.

26. The sterile surgical tray system of claim 1, wherein the rack system further comprises a vacuum source coupled to the rack system, wherein the vacuum source is configured to be controlled by the at least one controller in the sterile surgical tray.

27. The sterile surgical tray system of claim 26, wherein the vacuum source is coupled to the sterile surgical tray.

28. The sterile surgical tray system of claim 27, wherein at least one of the plurality of surgical instruments is configured to communicate with the vacuum source.

29. The sterile surgical tray system of claim 1, wherein the sterile surgical tray is disposable and the rack system is reusable.

30. The sterile surgical tray system of claim 1, wherein the sterile surgical tray is packaged in a sterile kit.

31. The sterile surgical tray system of claim 1, wherein the communication between the sterile surgical tray and the rack system is through a wired link.

32. The sterile surgical tray system of claim 1, wherein the communication between the sterile surgical tray and the rack system is through a wireless link.

* * * * *